United States Patent
Weber et al.

(10) Patent No.: US 8,333,795 B2
(45) Date of Patent: Dec. 18, 2012

(54) BULGING BALLOON FOR BIFURCATION CATHETER ASSEMBLY AND METHODS

(75) Inventors: Jan Weber, Maastricht (NL); James M. Anderson, Fridley, MN (US); Karl Jagger, Deephaven, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 303 days.

(21) Appl. No.: 12/199,674

(22) Filed: Aug. 27, 2008

(65) Prior Publication Data
US 2009/0163879 A1 Jun. 25, 2009

Related U.S. Application Data

(60) Provisional application No. 60/968,228, filed on Aug. 27, 2007.

(51) Int. Cl.
*A61F 2/84* (2006.01)
(52) U.S. Cl. .................. 623/1.11; 606/194; 604/103.07
(58) Field of Classification Search .................. 606/159, 606/108, 191–200; 623/1.11–1.54; 604/103.05, 604/103.08, 103.09, 103.06, 103.07
See application file for complete search history.

(56) References Cited

U.S. PATENT DOCUMENTS

| | | | |
|---|---|---|---|
| 4,490,421 A | 12/1984 | Levy | |
| 4,906,244 A | 3/1990 | Pinchuk et al. | |
| 4,950,227 A | 8/1990 | Savin et al. | |
| 4,950,239 A | 8/1990 | Gahara et al. | |
| 5,108,416 A | 4/1992 | Ryan et al. | |
| 5,250,069 A | 10/1993 | Nobuyoshi et al. | |
| 5,257,974 A * | 11/1993 | Cox | 604/103.05 |
| 5,264,260 A | 11/1993 | Saab | |
| 5,270,086 A | 12/1993 | Hamlin | |
| 5,304,121 A | 4/1994 | Sahatjian | |
| 5,328,468 A | 7/1994 | Kaneko et al. | |
| 5,344,400 A | 9/1994 | Kaneko et al. | |
| 5,470,313 A * | 11/1995 | Crocker et al. | 604/103.07 |
| 5,500,180 A | 3/1996 | Anderson et al. | |

(Continued)

FOREIGN PATENT DOCUMENTS
EP  1595569  11/2005
(Continued)

OTHER PUBLICATIONS

U.S. Appl. No. 61,018,043 to Donald Maim et al, filed Dec. 31, 2007, 55 pp.

*Primary Examiner* — Kathleen Sonnett
(74) *Attorney, Agent, or Firm* — Seager, Tufte & Wickhem, LLC

(57) ABSTRACT

A catheter assembly adapted to treat a vessel bifurcation. A balloon member of the catheter assembly includes a main body portion and a cylindrical shaped bulge portion that extends radially outward from the main body portion. The bulge portion extends around a circumference of the main body portion. A stent of the catheter assembly is typically mounted to the balloon member. When treating the vessel bifurcation, the catheter assembly is positioned with the bulge portion aligned axially relative to an ostium of the branch vessel. The balloon member is inflated to expand a portion of the stent into the branch vessel. The circumferential construction of the bulge portion of the balloon member reduces the need for radial (rotational) alignment of the balloon member relative to the ostium of the branch vessel.

5 Claims, 25 Drawing Sheets

U.S. PATENT DOCUMENTS

| | | | |
|---|---|---|---|
| 5,556,383 | A | 9/1996 | Wang et al. |
| 5,556,413 | A | 9/1996 | Lam |
| 5,683,451 | A * | 11/1997 | Lenker et al. ............... 623/1.11 |
| 5,776,141 | A * | 7/1998 | Klein et al. .................. 623/1.11 |
| 5,797,877 | A | 8/1998 | Hamilton et al. |
| 5,897,588 | A * | 4/1999 | Hull et al. ................... 623/1.15 |
| 5,944,726 | A | 8/1999 | Blaeser et al. |
| 5,954,706 | A | 9/1999 | Sahatjian |
| 5,980,530 | A | 11/1999 | Willard et al. |
| 6,120,847 | A | 9/2000 | Yang et al. |
| 6,146,356 | A | 11/2000 | Wang et al. |
| 6,156,373 | A | 12/2000 | Zhong et al. |
| 6,210,429 | B1 | 4/2001 | Vardi et al. |
| 6,261,305 | B1 * | 7/2001 | Marotta et al. ............... 606/200 |
| 6,270,522 | B1 | 8/2001 | Simhambhatla et al. |
| 6,325,826 | B1 | 12/2001 | Vardi et al. |
| 6,358,556 | B1 | 3/2002 | Ding et al. |
| 6,585,747 | B1 * | 7/2003 | Limon et al. .................. 606/198 |
| 6,692,483 | B2 | 2/2004 | Vardi et al. |
| 6,706,062 | B2 | 3/2004 | Vardi et al. |
| 6,913,619 | B2 | 7/2005 | Brown et al. |
| 6,942,680 | B2 | 9/2005 | Grayzel et al. |
| 6,945,993 | B2 | 9/2005 | Kveen et al. |
| 7,220,275 | B2 | 5/2007 | Davidson et al. |
| 7,223,283 | B2 | 5/2007 | Chouinard |
| 7,226,472 | B2 | 6/2007 | Pederson et al. |
| 7,553,324 | B2 * | 6/2009 | Andreas et al. .............. 623/1.12 |
| 2002/0010489 | A1 | 1/2002 | Grayzel et al. |
| 2003/0028211 | A1 | 2/2003 | Crocker et al. |
| 2005/0027248 | A1 | 2/2005 | Suzuki et al. |
| 2005/0080474 | A1 * | 4/2005 | Andreas et al. .............. 623/1.11 |
| 2005/0216047 | A1 * | 9/2005 | Kumoyama et al. .......... 606/191 |
| 2005/0251195 | A1 | 11/2005 | Wang |
| 2005/0273149 | A1 | 12/2005 | Tran et al. |
| 2006/0036263 | A1 | 2/2006 | Stinson |
| 2006/0045901 | A1 | 3/2006 | Weber |
| 2006/0074476 | A1 | 4/2006 | Holman et al. |
| 2006/0178685 | A1 * | 8/2006 | Melsheimer .................. 606/159 |
| 2006/0206188 | A1 | 9/2006 | Weber et al. |
| 2007/0203562 | A1 | 8/2007 | Malewicz et al. |
| 2007/0233270 | A1 | 10/2007 | Weber et al. |
| 2007/0239257 | A1 | 10/2007 | Weber et al. |
| 2008/0065188 | A1 | 3/2008 | Pallazza |
| 2008/0097464 | A1 | 4/2008 | Benson et al. |
| 2009/0069878 | A1 | 3/2009 | Weber et al. |

FOREIGN PATENT DOCUMENTS

| | | |
|---|---|---|
| WO | 2005/041810 | 5/2005 |
| WO | 2006036263 | 4/2006 |
| WO | 2006042260 | 4/2006 |
| WO | 2006074476 | 7/2006 |
| WO | 2007/136637 | 11/2007 |
| WO | 2009/029674 | 3/2009 |

* cited by examiner

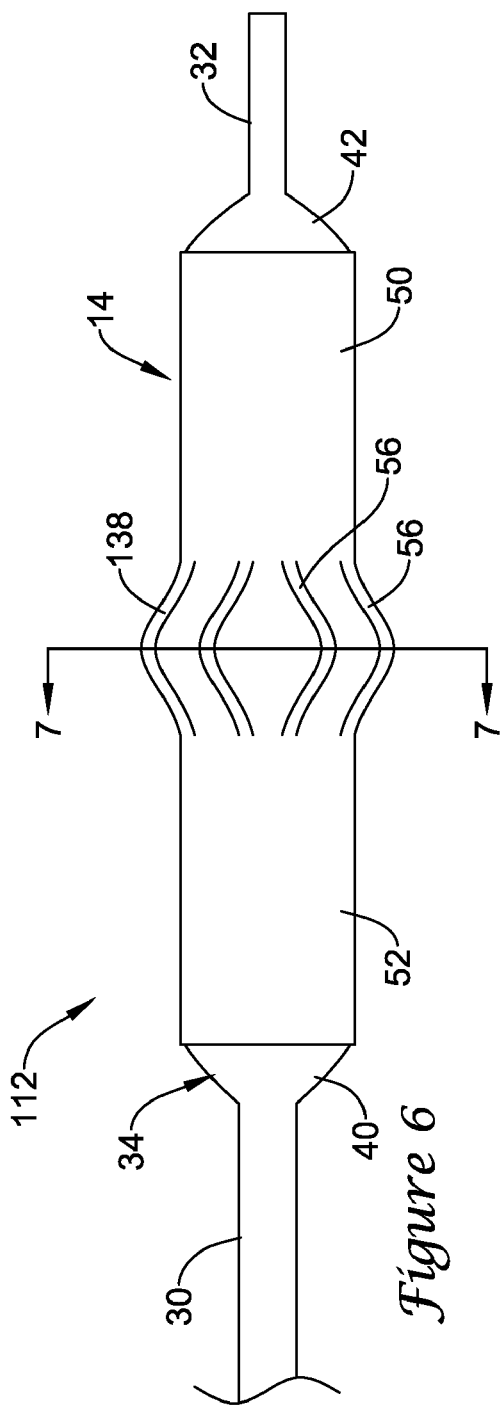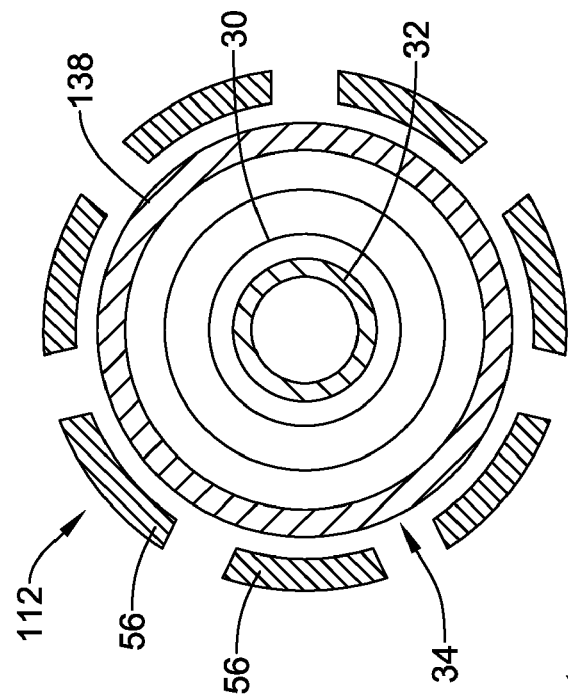

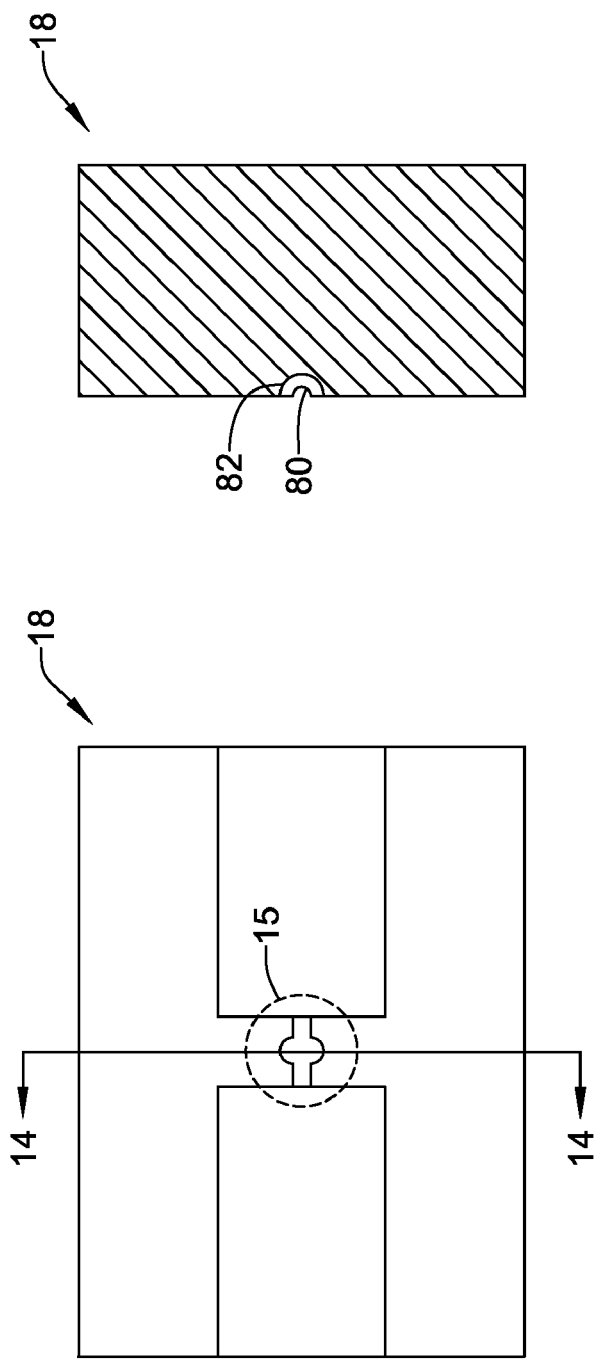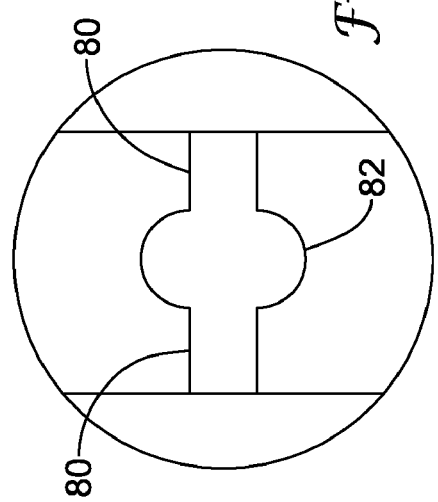
Figure 13
Figure 14
Figure 15

BULGING BALLOON FOR BIFURCATION CATHETER ASSEMBLY AND METHODS

RELATED APPLICATION

This application claims the benefit of U.S. Provisional Application Ser. No. 60/968,228, filed on Aug. 27, 2007, the entire disclosure of which is incorporated herein by reference.

TECHNICAL FIELD

This disclosure relates to catheter assemblies configured for treatment of a vessel bifurcation. Example arrangements provide for a bulge balloon member used with a catheter assembly.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body. Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves treating with a stent the area of the vessel bifurcation surrounding the ostium into a branch vessel. Multiple guidewires systems have been used to treat a vessel bifurcation to help align features of the stent delivery system relative to the branch vessel. Because of the complexity of aligning multiple guide wires within a tortuous system, single wire systems are preferred. However, single wire systems and even many multiple wire systems require advancing a guidewire through the struts of a deployed stent to obtain access into the branch vessel. Systems and methods that address these and other challenges related to treating vessel bifurcation would be an advance in the art.

SUMMARY OF THE DISCLOSURE

The present disclosure relates to balloon members and catheter assemblies used to treat a vessel bifurcation. An example balloon member includes a main body portion and a cylindrical shaped bulge portion that extends radially outward from the main body portion. The bulge portion typically extends around a circumference of the main body portion. The stent includes a distal open end, a proximal open end, and expandable structure positioned at a location between the distal and proximal open ends that is configured to extend radially outward relative to a sidewall of the stent. The expandable structure typically extends around a circumference of the stent sidewall. When treating the vessel bifurcation, the stent is positioned with the expandable structure aligned axially relative to an ostium of the branch vessel (also referred to as a branch vessel opening). The balloon member is inflated to expand the expandable structure into the branch vessel. The circumferential construction of the bulge portion of the balloon member reduces the need for radial (rotational) alignment of a specific portion of the balloon member relative to the ostium of the branch vessel.

Expansion of the expandable structure of the stent into the branch vessel can provide increased spacing between strut members of the stent. The increased spacing between the strut members provides improved ease for the physician to advance a guidewire through the stent sidewall and into the branch vessel. With a guidewire advanced through the stent sidewall and into the branch vessel, further treatment of the branch vessel can be performed using a balloon member and/or branch stent that further expands the expandable structure into engagement with the branch vessel.

There is no requirement that an arrangement include all features characterized herein to obtain some advantage according to this disclosure.

BRIEF DESCRIPTION OF THE DRAWINGS

FIG. 6 is a schematic side view of the balloon catheter assembly shown in FIG. 4, wherein the balloon member is in an inflated state;

FIG. 7 is a schematic cross-sectional view of the balloon catheter assembly shown in FIG. 6 taken along cross-sectional indicators 7-7;

FIG. 13 is a top view of the balloon mold shown in FIG. 12;

FIG. 14 is a cross-sectional view of the balloon mold shown in FIG. 13 taken along cross-sectional indicators 14-14;

FIG. 15 is a close-up view of the balloon bulge portion of the balloon mold shown in FIG. 13;

DETAILED DESCRIPTION

Figure 1:
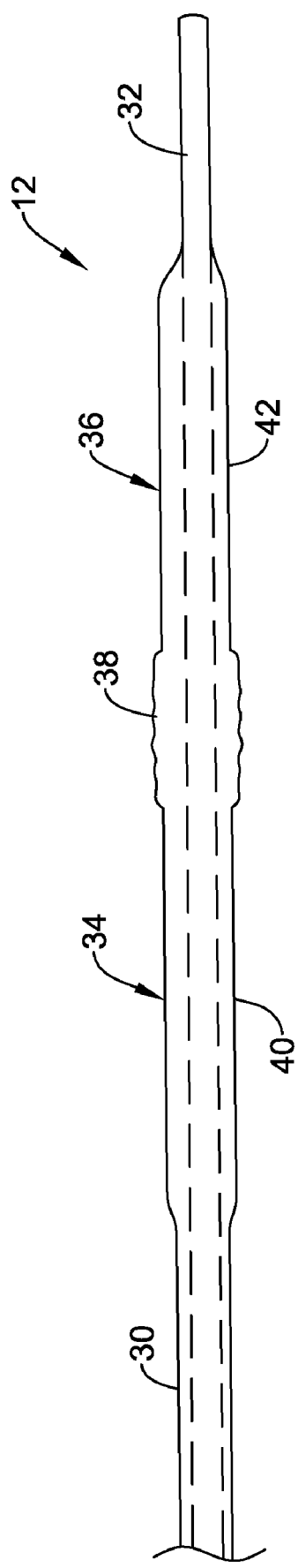
FIG. 1 is a schematic side view of balloon catheter for a stent delivery system constructed according to principles of the present disclosure, wherein the balloon includes a circumferential bulge portion.

This disclosure relates to bifurcation treatment systems, catheter assemblies, stent delivery systems, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The example catheter assemblies, balloon members, stents and stent delivery systems disclosed herein provide for treatment of a vessel bifurcation using a single guidewire arrangement. In one example, a balloon member of a catheter assembly can be used to expand a portion of the stent from the main vessel radially outward into the branch vessel. The balloon member is positioned within the main vessel axially aligned with the ostium or opening into the branch vessel. The shape and size of the expanding features of the balloon are substantially the same around a circumference of the balloon member. Thus, the radial or rotated position of the balloon relative to the ostium is generally irrelevant. The balloon member can be used in conjunction with a particular stent construction that has a region that is more conducive to expansion into the branch vessel at any given rotated position relative to the ostium of the branch vessel.

After expanding at least a portion of the stent radially outward into the branch vessel, a guidewire can be passed through the radially expanded portion of the stent into the branch vessel to assist in further expanding the stent to treat the vessel bifurcation. The guidewire used to pass through the radial expanded portion of the stent and into the branch vessel can be the same guidewire that was used for deployment of the stent within the main vessel. An additional vessel treatment device such as a post-dilation balloon catheter can be advanced along the guidewire, through the radially expanded portion of the stent and into the branch vessel.

Various balloon member constructions, catheter assemblies, and stents, and related methods of treating a vessel bifurcation are described in further detail below.

Figure 2:
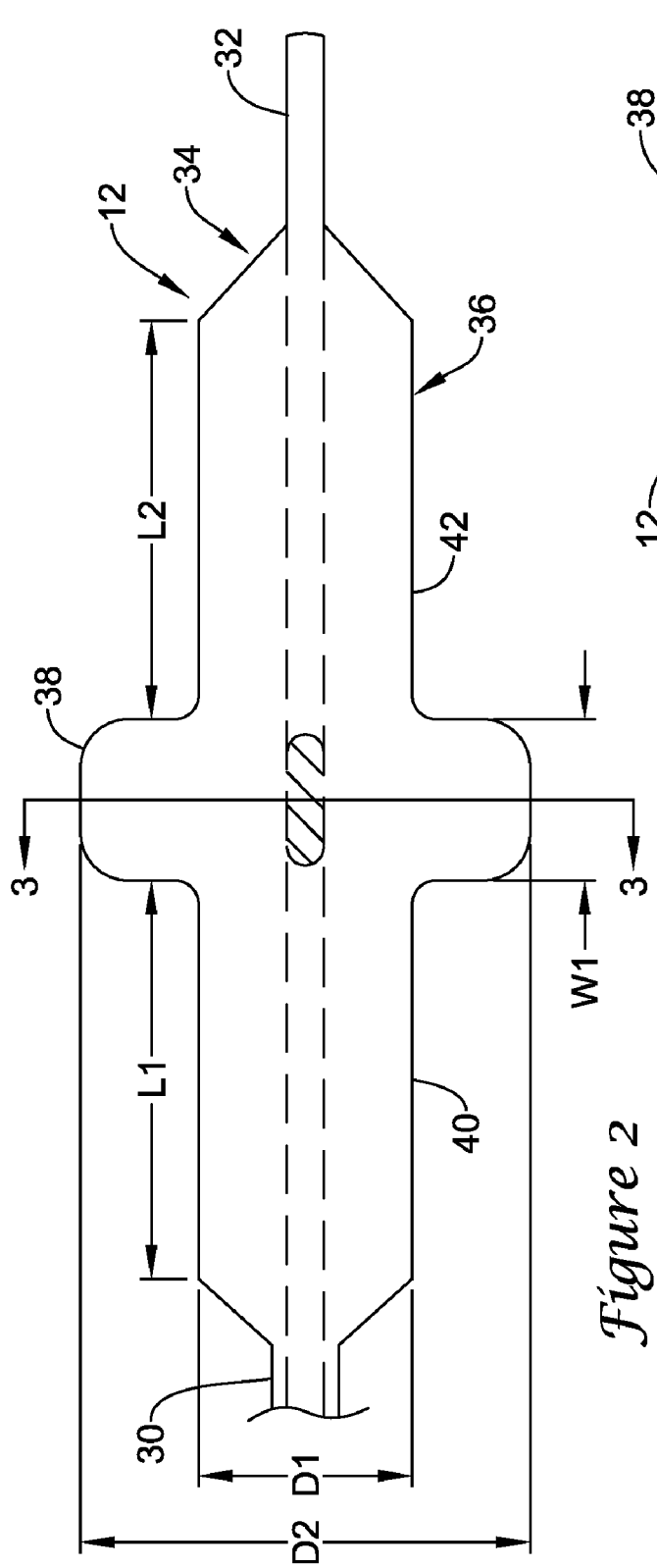
FIG. 2 is a schematic side view of the balloon catheter shown in FIG. 1 with the balloon in an inflated stated.
Figure 3:
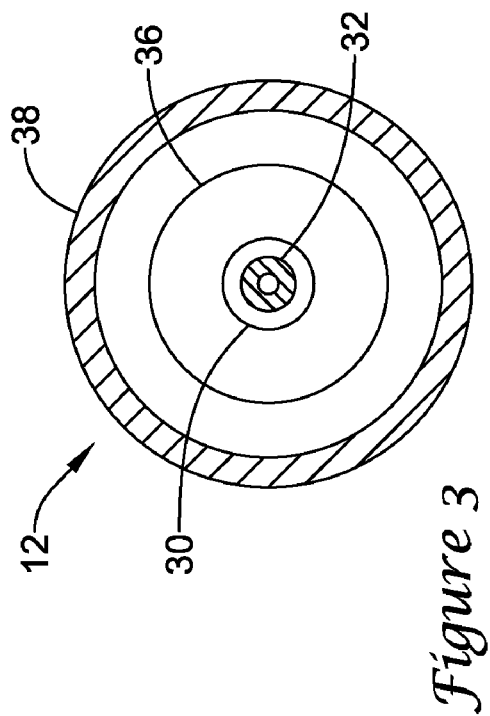
FIG. 3 is a cross-sectional view of a balloon catheter shown in FIG. 2 taken along cross-sectional indicators 3-3.

The Example Catheter Assembly of FIGS. 1-3

Referring now to FIGS. 1-3, an example main catheter branch 12 is shown and described. Main catheter branch 12 includes a shaft 30, a guidewire housing 32, and a balloon member 34. The balloon member 34 includes a main balloon portion 36 and a bulge portion 38. The main balloon portion 36 is divided into a proximal end portion 40 positioned proximal of the bulge portion 38, and a distal end portion 42 positioned distal of the bulge portion 38.

FIG. 1 illustrates that main catheter branch 12 with the balloon member 34 in a deflated state. FIGS. 2 and 3 illustrate the main balloon member 34 in an inflated state. The proximal and distal end portions 40, 42 of the inflated balloon member define a balloon diameter D1. The portions 40, 42 can have lengths L1, L2, respectively. The diameter D1 can be the same for each of the portions 40, 42. Alternatively, each portions 40, 42 can have a different value for diameter D1. The lengths L1, L2 can be the same or different in alternative arrangements. The inflated bulge portion 38 defines a diameter D2, wherein the diameter D2 is greater than the diameter D1. The bulge portion 38 also has a width W1 defined in an axial direction along the balloon member 34.

The cross-sectional view of FIG. 3 illustrates that the bulge portion 38 has a relatively constant diameter D2 around the circumference of the main balloon portion 36. As will be described in further detail below, the bulge portion 38 can be used to treat a vessel bifurcation by extending from within the main vessel of the vessel bifurcation radially outward through the branch vessel ostium regardless of the radial orientation of the bulge portion 38 relative to the ostium of the branch vessel. In one example, the diameter D1 is in the range of about 1 to about 3 mm, or in another example, about 1.5 to about 2.5 mm. The diameter D2 can be in the range of about 2 to about 6 mm, or in another example, about 3 to about 5 mm. The diameter D2 can also be defined in relationship to the size of D1. For example, 02 can be in the range of about 25 to about 200% greater than D1, and in another example, about 50 to about 150% the size of D1.

The width W1 is typically in the range of about 0.5 to about 4 mm, and in one example, about 1 to about 1.5 mm. The size dimensions D1, D2, W can vary depending on, for example, the size of the vessels being treated at the vessel bifurcation including the size of the ostium into the branch vessel. Typically, each of the lengths L1, L2 of portions 40, 42, respectively, is between about 2 mm and about 10 mm. The value of L1 and L2 can be the same or different.

The bulge portion 38 can be formed in the balloon member 34 using a molding process. FIGS. 12-15 illustrate an example portion of a balloon mold that could be used to form the bulge portion 38 in the balloon member 34. The balloon mold body 18 includes a main balloon cavity portion 80 sized to receive a length of hollow cylindrical catheter material. A bulge portion cavity 82 is defined in the balloon mold body

18. A pair of mold inserts (not shown) can be positioned within mold insert recesses 81A, B on opposing sides of the bulge portion cavity 82. Each of the mold inserts (not shown) can define an additional length of balloon cavity aligned with the main balloon cavity portion 80.

Commercial high strength balloons having wall strengths in excess of 20,000 psi, have been formed of a wide variety of polymeric materials, including PET, nylons, polyurethanes and various block copolymer thermoplastic elastomers. U.S. Pat. Nos. 4,490,421 and 5,264,260, which are incorporated herein by reference, describe PET balloons. U.S. Pat. Nos. 4,906,244 and 5,328,468, which are incorporated herein by reference, describe polyamide balloons. U.S. Pat. Nos. 4,950,239 and 5,500,180, which are incorporated herein by reference, describe balloons made from polyurethane block copolymers. U.S. Pat. Nos. 5,556,383 and 6,146,356, which are incorporated herein by reference, describe balloons made from polyether-block-amide copolymers and polyester-block-ether copolymers. U.S. Pat. No. 6,270,522, which is incorporated herein by reference, describes balloons made from polyester-block-ether copolymers of high flexural modulus. U.S. Pat. No. 5,344,400, which is incorporated herein by reference, describes balloons made from polyarylene sulfide. All of these balloons are produced from extruded tubing of the polymeric material by a blow-forming radial expansion process. U.S. Pat. Nos. 5,250,069; 5,797,877; and 5,270,086, which are incorporated herein by reference, describe still further materials which may be used to make such balloons. A further list of balloon and catheter shaft materials is provided below.

An example method of producing a balloon such as the balloon member 34 includes application of heat, internal pressure, and axial tensioning on a length of hollow cylindrical catheter material captured within the main balloon cavity portion 80 and bulge portion cavity 82. The resulting structure of this method provides the main balloon portion 36 and bulge portion 38 in the balloon member 34.

An alternate method could include, after an initial mold process of forming the main balloon portion 36 (i.e., a main balloon portion having a diameter of about 4 to 5 mm), creating in a secondary step the bulge portion 38 in a secondary molding process. The secondary molding process can include selectively heating the balloon material of the main balloon portion 36 and shrinking or necking the balloon material down to a desired diameter (e.g., about 2 to 3 mm in diameter) on the proximal or distal ends of the balloons such to create the bulge. This secondary process can include heating the balloon material to a certain temperature that makes the balloon material soft enough so for the balloon material to shrink down. This secondary process can be done with direct contact of heated elements such as stainless steel or Teflon. Alternatively, the secondary process can be accomplished by applying heated air to the balloon material allowing the balloon material to recover from the initial molding expansion and causing the diameter to abruptly decrease.

The Example Catheter Assembly of FIGS. 4-7

Referring now to FIGS. 4-7, an example main catheter branch 112 is described. The main catheter branch 112 includes a shaft 30, a guidewire housing 32, a balloon member 134, and a sleeve assembly 14. The balloon member 134 includes a proximal end portion 40, a distal end portion 42, and a bulge portion 138. The bulge portion 138 differs from the bulge portion 38 described with reference to FIGS. 1-3 above in that the bulge portion 138 is not molded into the balloon member 134. The bulge portion 138 results from the construction of the sleeve assembly 14 that permits further expansion of the balloon member 134 in the area of the bulge portion 138 while restricting expansion of the proximal and distal end portions 40, 42. Typically, the balloon member 134 shown in FIGS. 4-7 would have a constant diameter along a length of the balloon member 134 and around a circumference of the balloon member 134 if the sleeve assembly 14 was not positioned on the balloon member 134.

The sleeve assembly 14 includes a distal portion 50, a proximal portion 52, and a plurality of slits 54 that define a plurality of sleeve strips 56. The number of slits 54 and the radial spacing between the slits 54 around a circumference of the sleeve assembly 14 can vary to provide different numbers, shapes and sizes of the sleeve strips 56.

Figure 4:
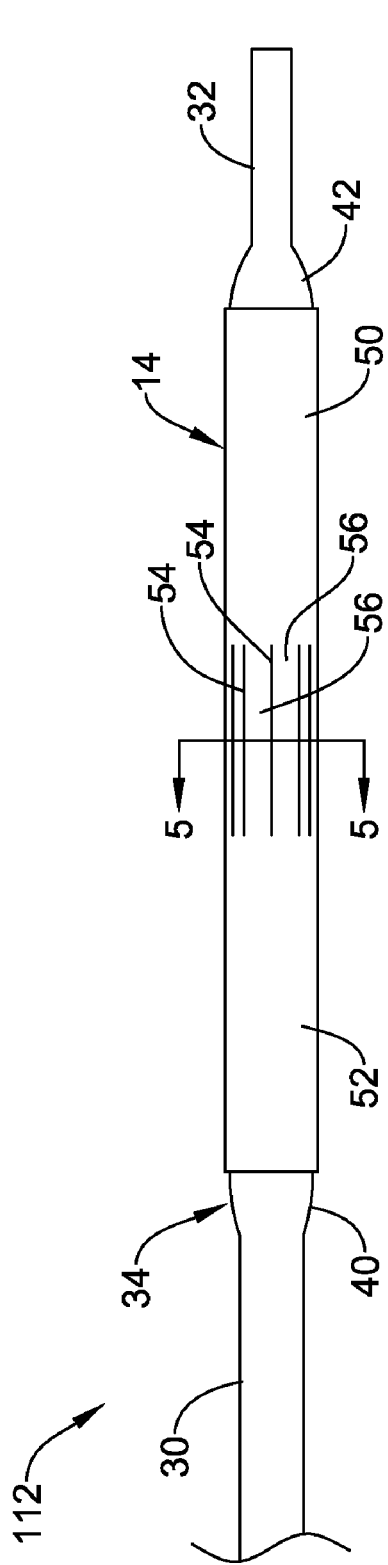
FIG. 4 is a schematic side view of another example balloon catheter assembly for use in a stent delivery system constructed in accordance with principles of the present disclosure, wherein the balloon catheter assembly includes a sheath having a plurality to provide an expandable portion.
Figure 5:
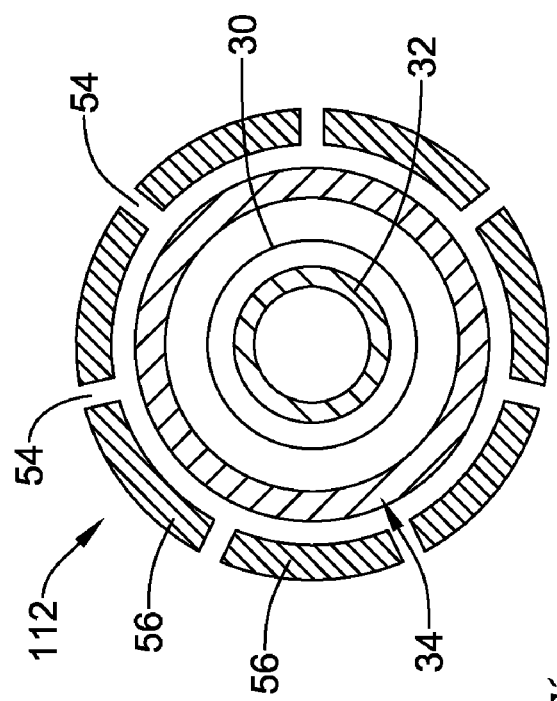
FIG. 5 is a schematic cross-sectional view of the balloon catheter assembly shown in FIG. 4 taken along cross-sectional indicators 5-5.

The sleeve assembly 14 include eight slits 54 equally spaced apart around a circumference of the sleeve assembly 14 to define seven sleeve strips 56. FIGS. 4 and 5 illustrate how the sleeve strips 56 are positioned adjacent to each other around a circumference of the balloon member 134 when the balloon member 134 is in a deflated state. FIGS. 6 and 7 illustrate how the sleeve strips 56 become spaced apart around a circumference of the bulge portion 138 of the balloon member 134 when the balloon member 134 is in an inflated state. The slits 54 permit bulging of the balloon member 134 around a circumference of the balloon member to form the bulge portion 138 in the area where the sleeve strips 56 are defined. The bulge portion 138 can function similar to the bulge portion 38 described with reference to FIGS. 1-3 in expanding portions of a stent in a radial outward direction into a branch vessel of a vessel bifurcation.

The sleeve assembly 14 can comprise elastic or inelastic materials. In one example, the sleeve assembly 14 comprises an elastic material such as polyurethane (e.g., Tecothane or Tecophilic) or silicone rubber. Typically, an unstrained dimension of an elastic tubular sleeve member is smaller than diameter D1 and, in some examples, smaller then the diameter of the deflated (i.e., folded) balloon as shown in FIG. 4.

Figure 8A:
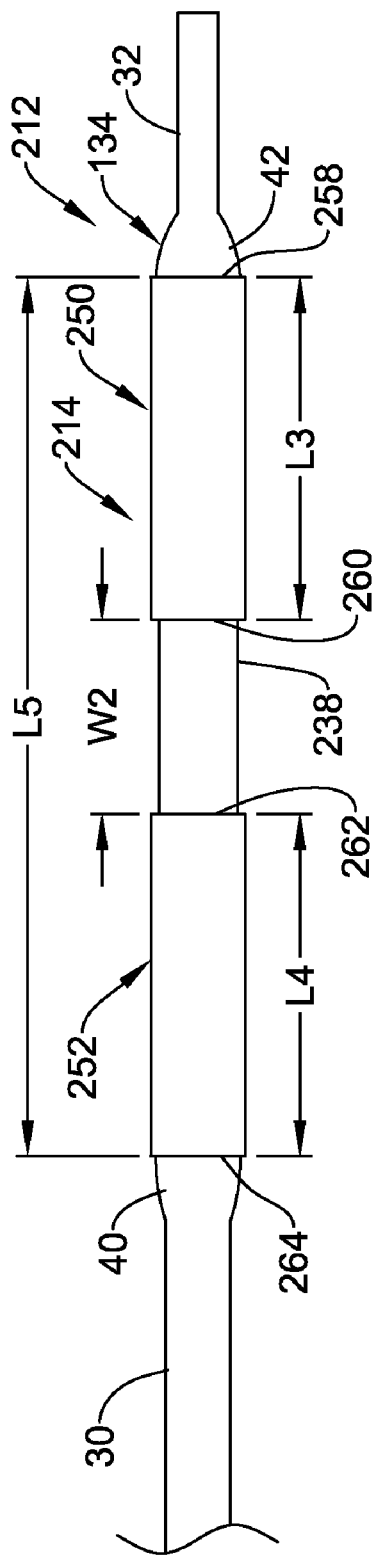
FIG. 8A is a schematic side view of another example balloon catheter assembly for use with a stent delivery system constructed according to principles of the present disclosure, wherein the sleeve includes distal and proximal members spaced apart to provide a circumferential bulge in the balloon when inflated.
Figure 8B:
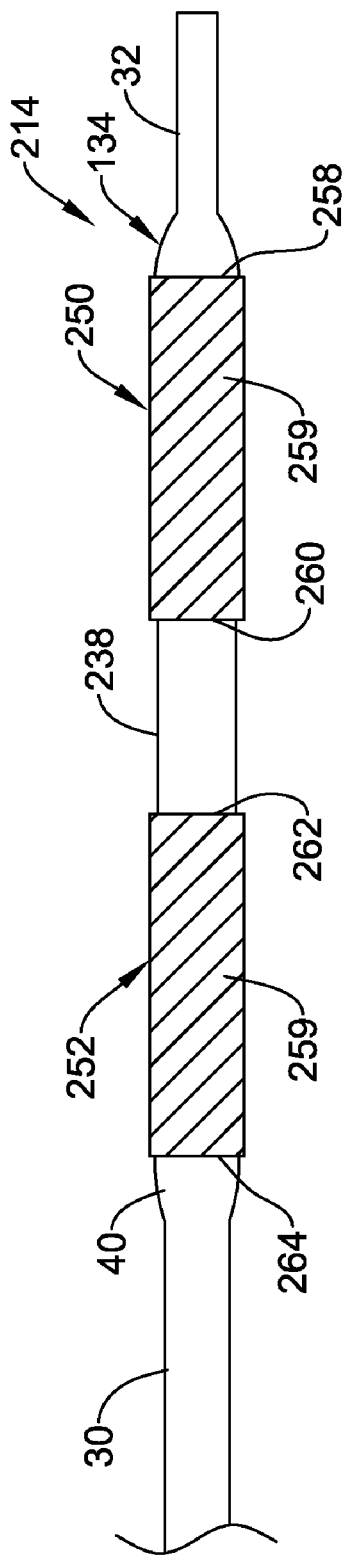
FIG. 8B is a schematic side view of the balloon catheter assembly shown in FIG. 8A wherein the sleeve portions include a spiral cut construction.
Figure 9:
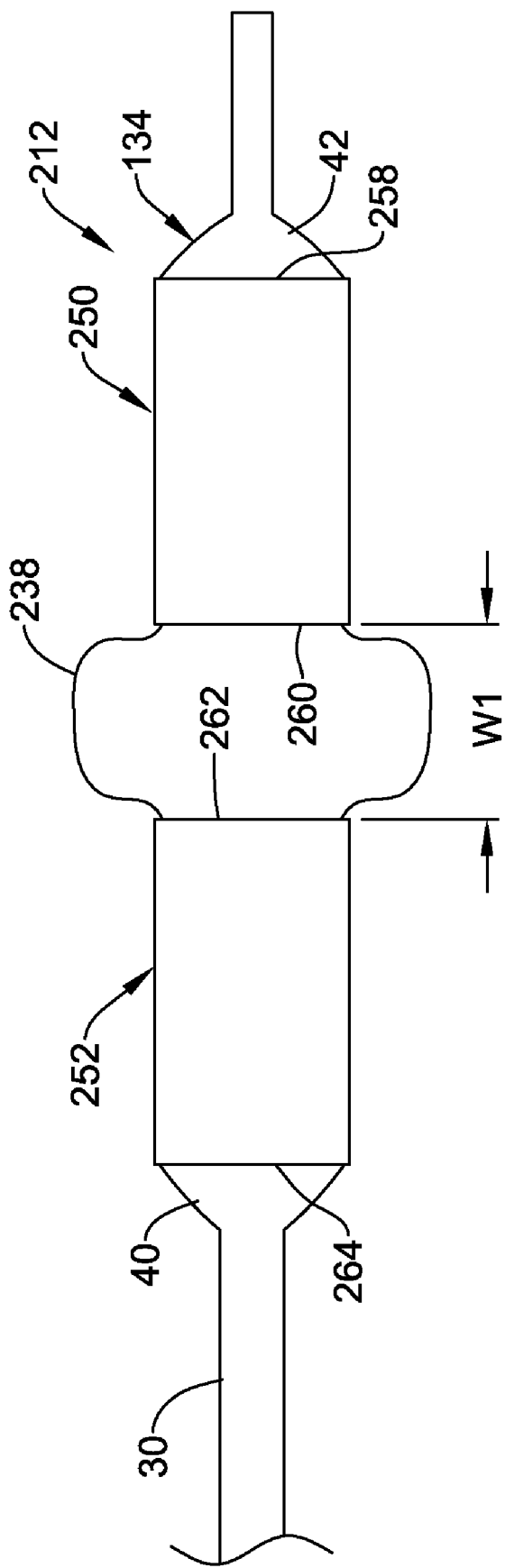
FIG. 9 is a schematic side view the balloon catheter assembly shown in FIG. 8A with the balloon in an inflated state.

The Example of FIGS. 8A-9

FIGS. 8A and 9 illustrate another example main catheter branch 212. The main catheter branch 212 includes a balloon member 134, and a sleeve assembly 214. The sleeve assembly 214 includes a distal portion 250 and a proximal portion 252. The distal portion 250 includes a distal end 258 and a proximal end 260, and has a length L3. The proximal portion 252 includes a distal end 262 and a proximal end 264, and has a length L4. The proximal end 260 of the distal portion 252 is axially spaced apart from the distal end 262 of the proximal portion 252. An axial spacing W2 between the distal and proximal portions 250, 252 prior to inflation of the balloon member 134 permits radial outward expansion of a bulge portion 238 in the balloon member 134 as the balloon member 134 is inflated (see FIG. 9).

The resulting width W1 of the bulge member 238 depends in part on the spacing W2 between proximal end 260 and distal end 262 before, during, and after inflation of the balloon member 134. The spacing W2 can vary depending on for example, a total length L5 of the balloon member 134, a size and shape of the main and branch vessels of the vessel bifurcation being treated with the main catheter branch 212, and the amount of compliance in the material used for the sleeve assembly 214. Typically, the total length of the spacing W2 plus the lengths L3, L4 of the sleeve assembly 214 is no greater than the total length L5 of the balloon member 134. Alternatively, the dimensions of spacing W2 and lengths L3, L4 result in the distal end 258 of sleeve member 250 extending distally beyond the distal end portion 42 of the balloon member 134, and the proximal end 264 of sleeve member 252 extending proximally beyond a proximal end portion 40 of the balloon member 134.

In some embodiments the proximal and distal ends 260, 262 can have a flared construction (not shown) that can assist in formation of the bulge portion 238 of the balloon member 134. Such flared portions can also help reduce incidence of damage to the balloon member 134 during inflation and deflation of the balloon member 134.

The distal and proximal portions 250, 252 of the sleeve assembly 214 can include at least one spiral cut 259. The spiral cut 259 can provide limited radial expansion of the distal and proximal portions 250, 252 that limits inflation and expansion of the balloon member 134 except in that area spaced between the proximal and distal ends 260, 262 where the bulge portion 238 is formed during inflation of the balloon member 134. The spiral cut 259 can also provide more flexibility for the catheter branch 212. Typically, the spiral cut 259 does not extend to the proximal ends 260, 264 and distal ends 258, 262 of the sleeve portions 250, 252 (see FIG. 8B).

The spiral cut 259 can provide improved column strength for increased "pushability" of the catheter branch 212 to a vessel bifurcation treatment site, high radial strength for expansion resistance of the balloon member 134, and yet good flexibility for tracking through tortuous anatomy. The spiral cut 259 can also help preserve a level of elastic contractive force upon balloon deflation that could purge the inflation media more rapidly from the bulge area and minimize the system profile "deflated bulk" upon withdrawal from the expanded stent section, thereby reducing the likelihood of needing unacceptable withdrawal forces.

Figure 10:
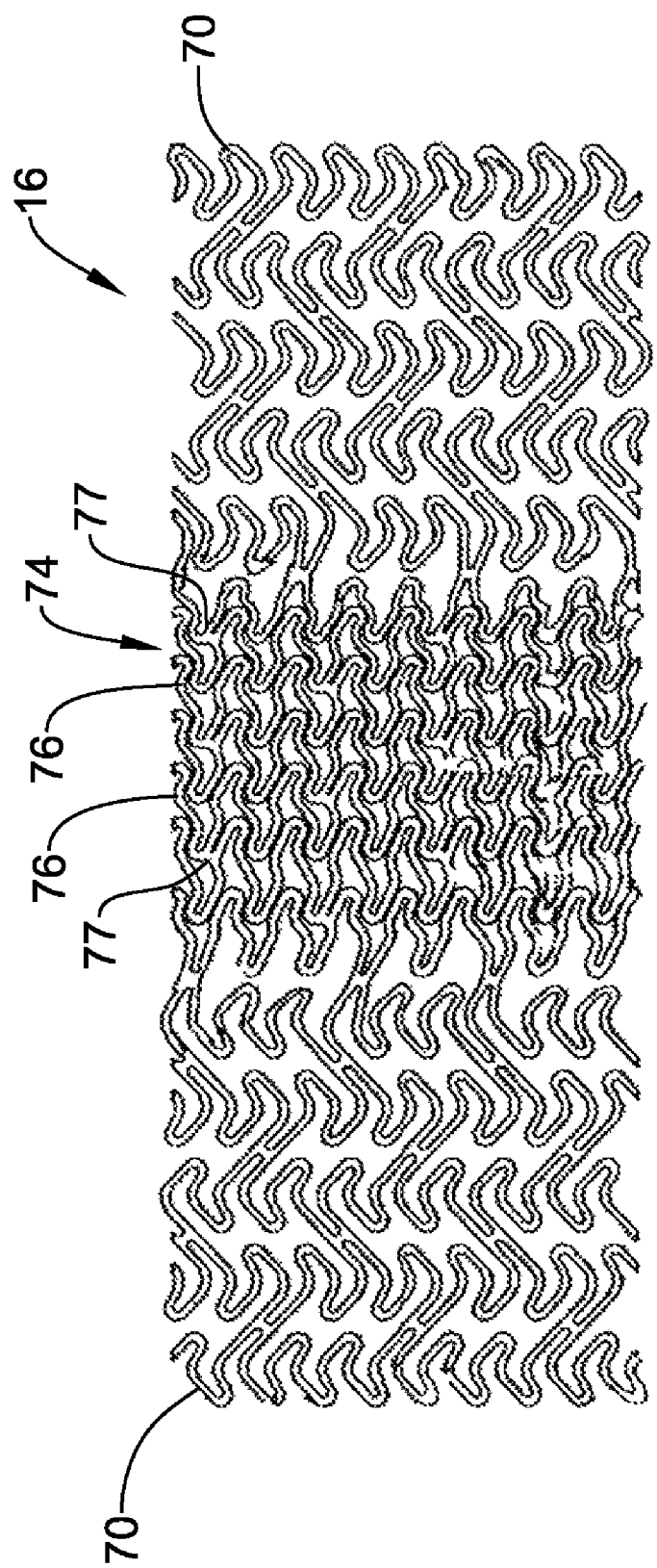
FIG. 10 is a schematic side view of an example stent member constructed for use with one of the balloon catheter assemblies shown in FIGS. 1-8B.
Figure 11:
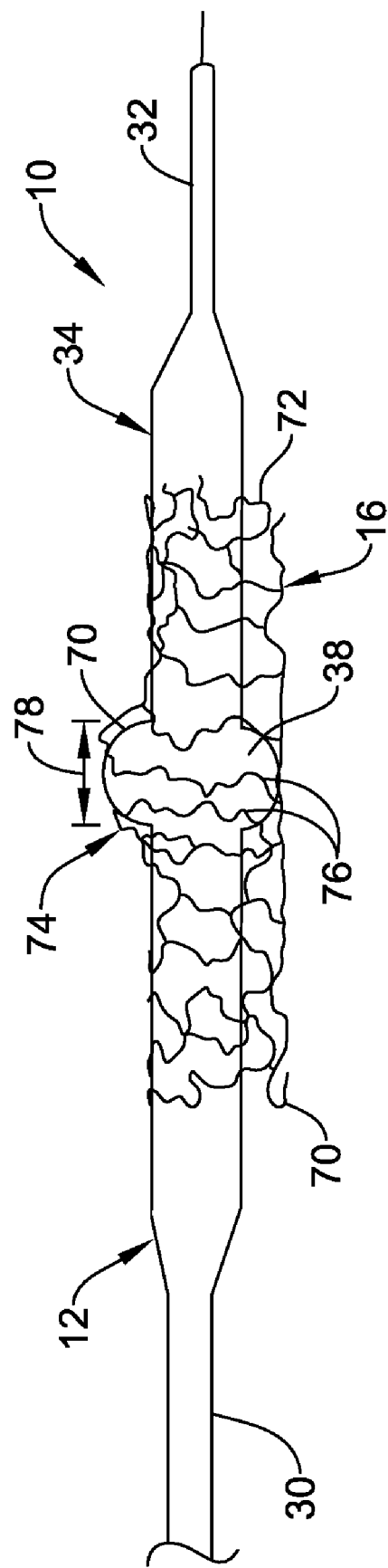
FIG. 11 is a schematic side view of the stent member shown in FIG. 10 being expanded with the balloon catheter assembly shown in FIGS. 1-3.
Figure 12:
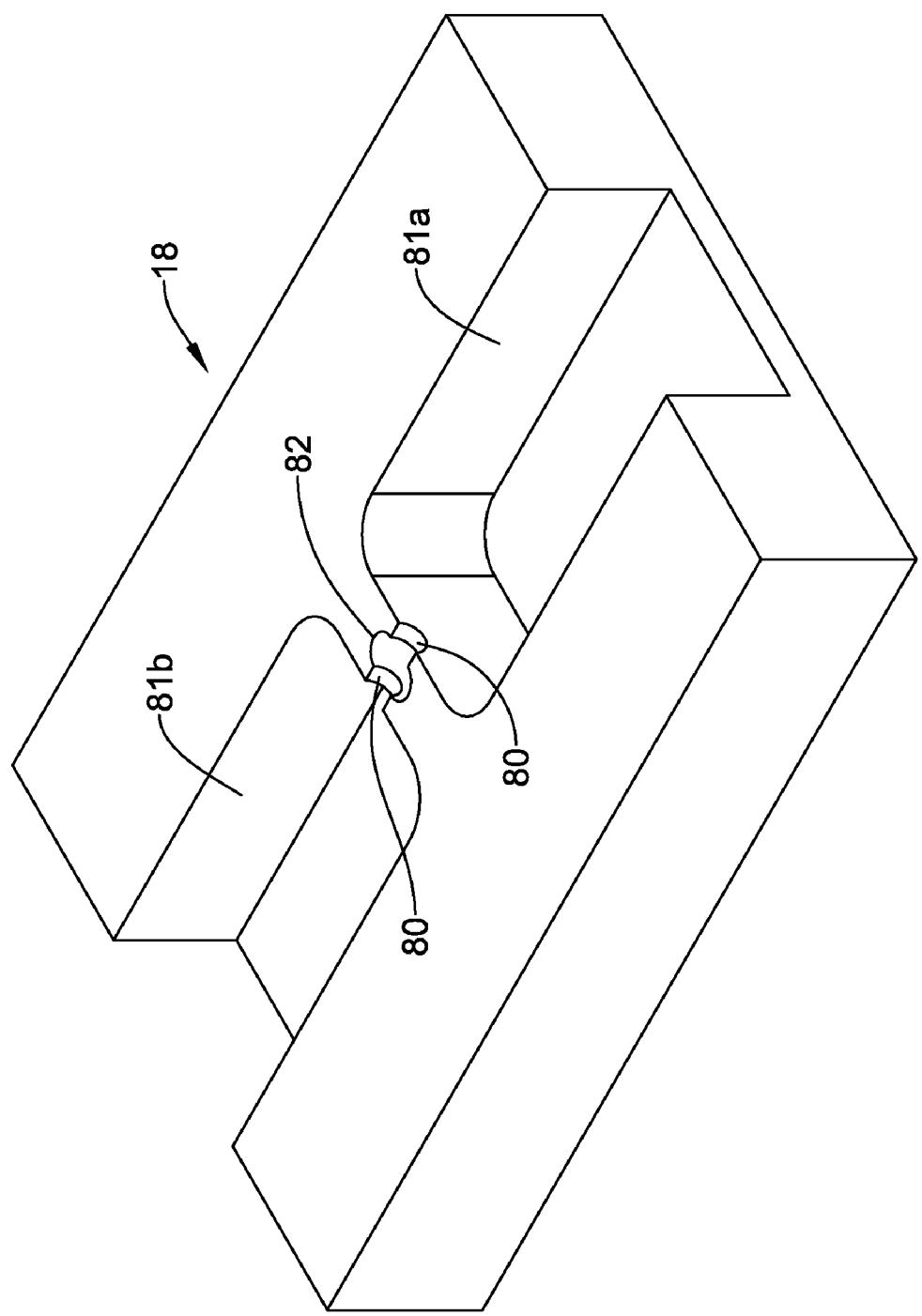
FIG. 12 is a schematic perspective view of an example balloon mold for use in forming the balloon catheter assembly shown in FIGS. 1-3.
Figure 16:
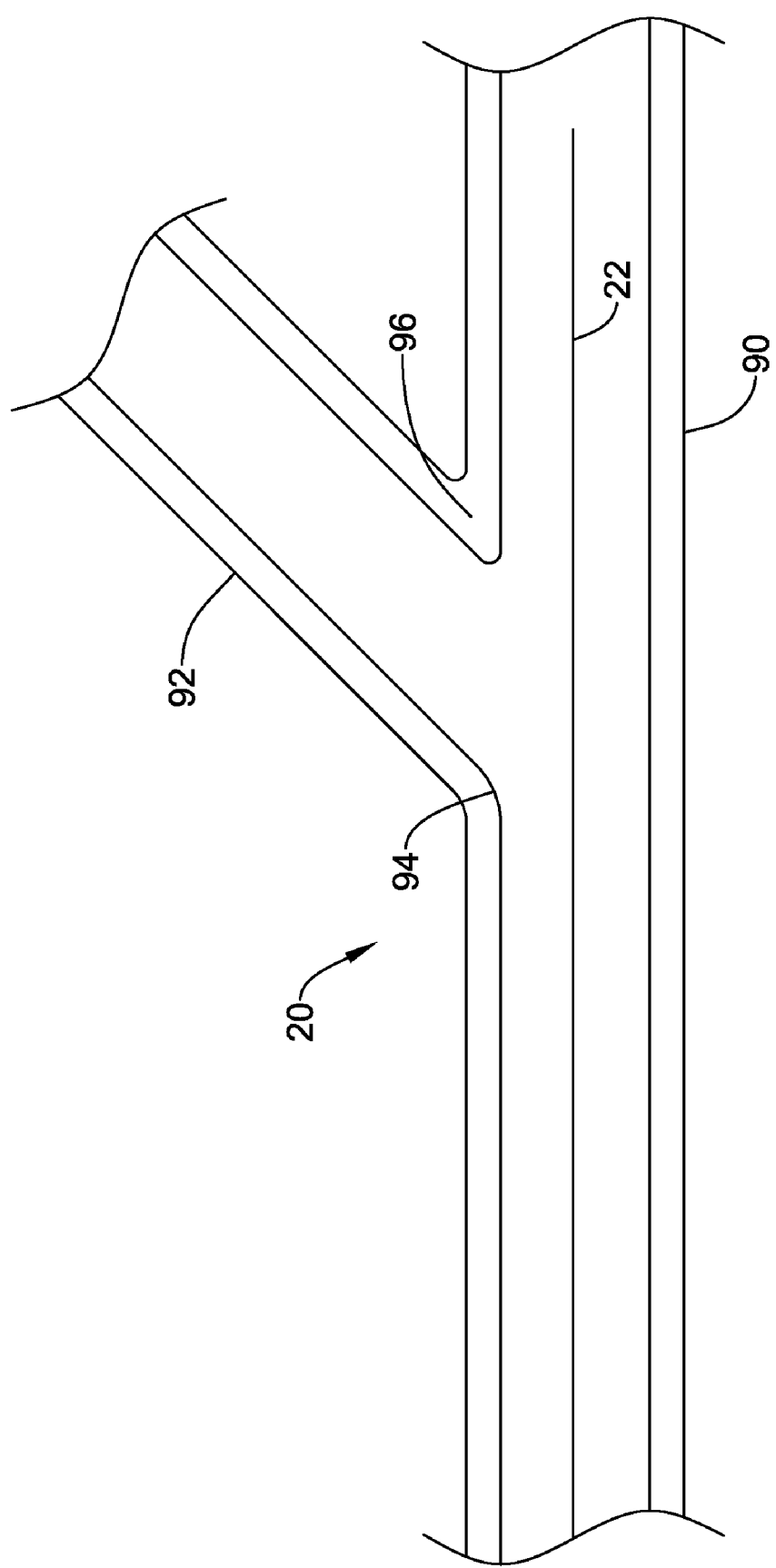
FIGS. 16-22 illustrate steps of an example method of treating a vessel bifurcation using the balloon catheter assembly of FIGS. 1-3 and a post-dilation balloon catheter.
Figure 17:
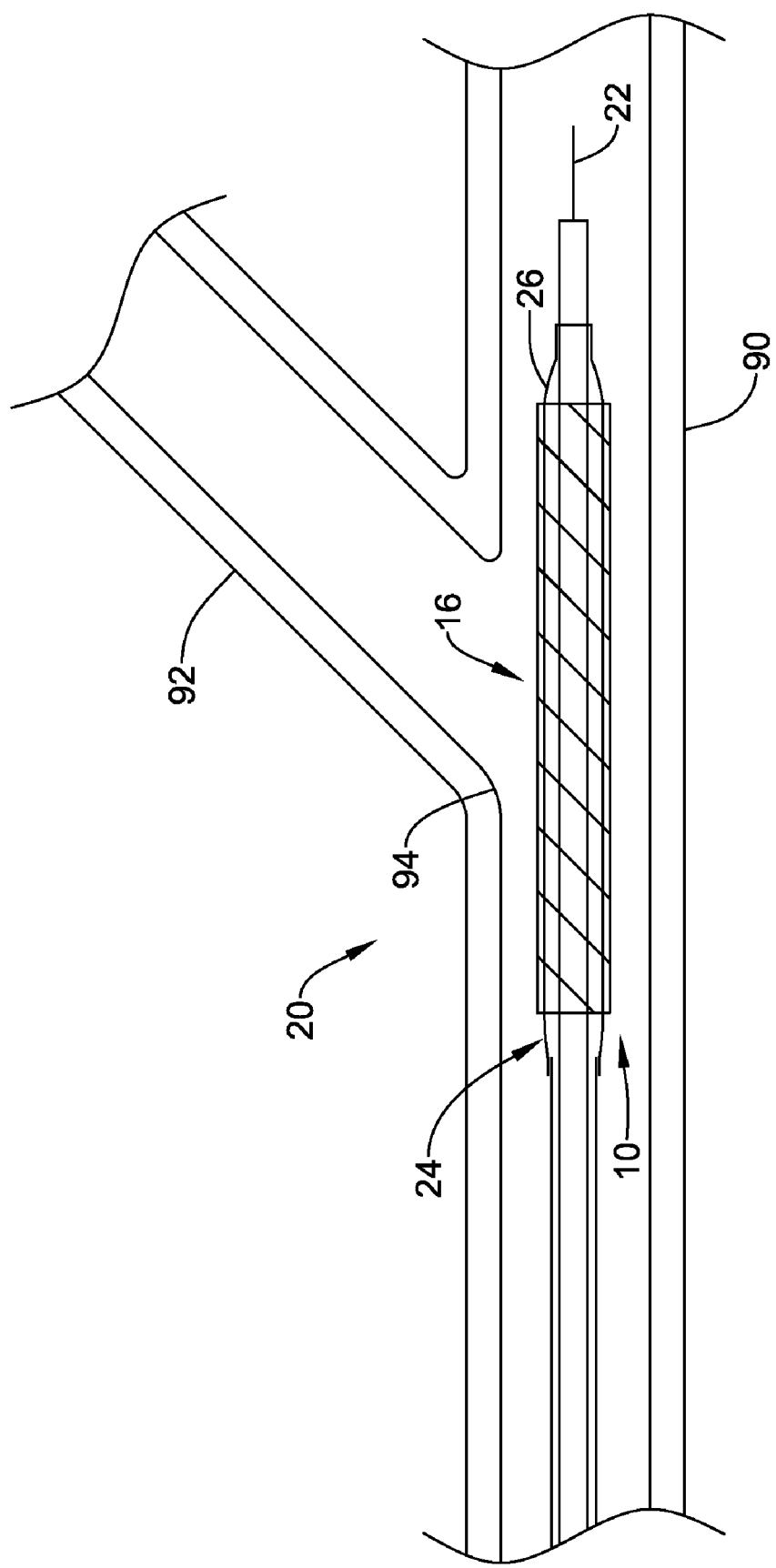
Figure 18:
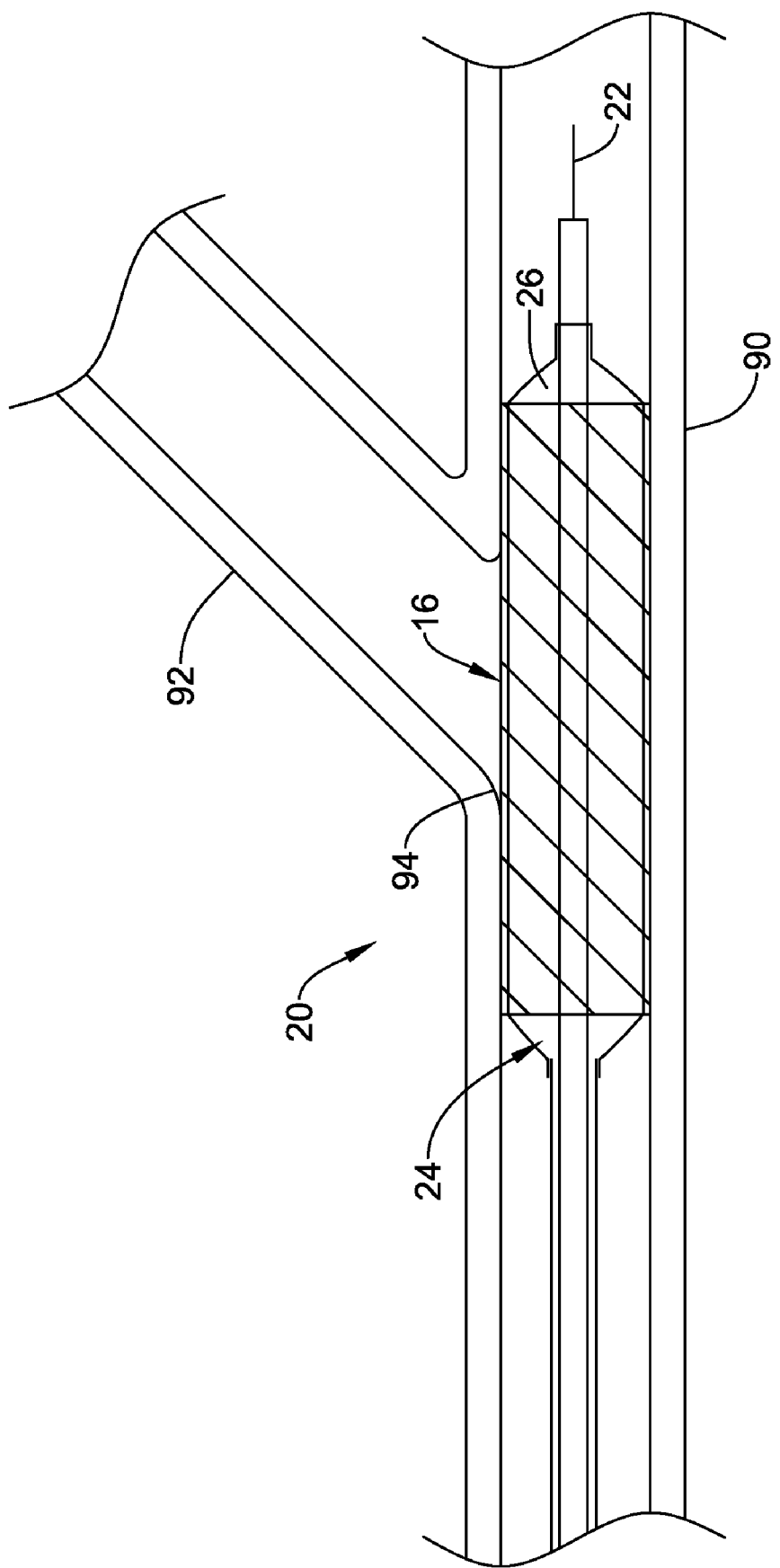

The Example Stent of FIGS. 10 and 11

FIG. 10 illustrates an example stent 16 for use with the main catheter branches disclosed herein for treatment of a vessel bifurcation. The stent 16 includes proximal and distal open ends 70, 72 and expandable structure zone 74, a plurality of rows of struts 76, and a plurality of connecting points 77 between the plurality of rows of struts 76.

The density of the rows of struts 76 and the limited number of connection points 77 provide for increased spacing of parts 78 of the struts 76 when the stent 16 expanded with a bulge portion 38 of a balloon member 34 as shown in FIG. 11. The spacing 78 provides for easier navigation of a guidewire through the struts 76 and into a branch vessel of a vessel bifurcation. The expandable structure zone 76 is intended to provide radially outward extended orientation of the struts 76 into the branch vessel at any location around a circumference of the stent 16. Thus, the radial orientation of the expandable structure zone 74 relative to an opening into the branch vessel is irrelevant as the stent 16 will perform equally at any radially rotated position.

Some example constructions for the stents 16 are disclosed in co-pending U.S. patent application Ser. No. 11/755,592, filed on May 30, 2007 and titled STENT WITH OVERLAP AND HIGH EXPANSION, and U.S. patent application Ser. No. 11/392,047, filed on Mar. 29, 2006 and titled STENT WITH OVERLAP AND HIGH EXPANSION, which are incorporated herein by reference.

The Treatment Method of FIGS. 16-22

FIGS. 16-22 illustrate an example method of treating a vessel bifurcation 20. The vessel bifurcation 20 includes a main vessel 90, a branch vessel 92, and ostium 94 defined as an opening from the main vessel 90 into the branch vessel 92, and a carina feature 96 at the intersection of the main and branch vessels 90, 92.

Initially, a guidewire 22 is advanced through the main vessel to a location distal of the ostium 94. A first catheter assembly 10 is then advanced over the guidewire 22 to a location spanning the ostium 94 of the branch vessel 92. The first catheter assembly 10 includes a secondary catheter branch 24 having a constant diameter balloon 26 upon which a stent 16 is positioned. Typically, the stent 16 is mounted to the balloon 26 using, for example, a crimping or a related way of releasably mounting the stent 16 to the balloon 26. The balloon 26 is then inflated to expand the stent 16 into engagement with the main vessel 90 on a side opposing the ostium 94 into the branch vessel 92.

Figure 19:
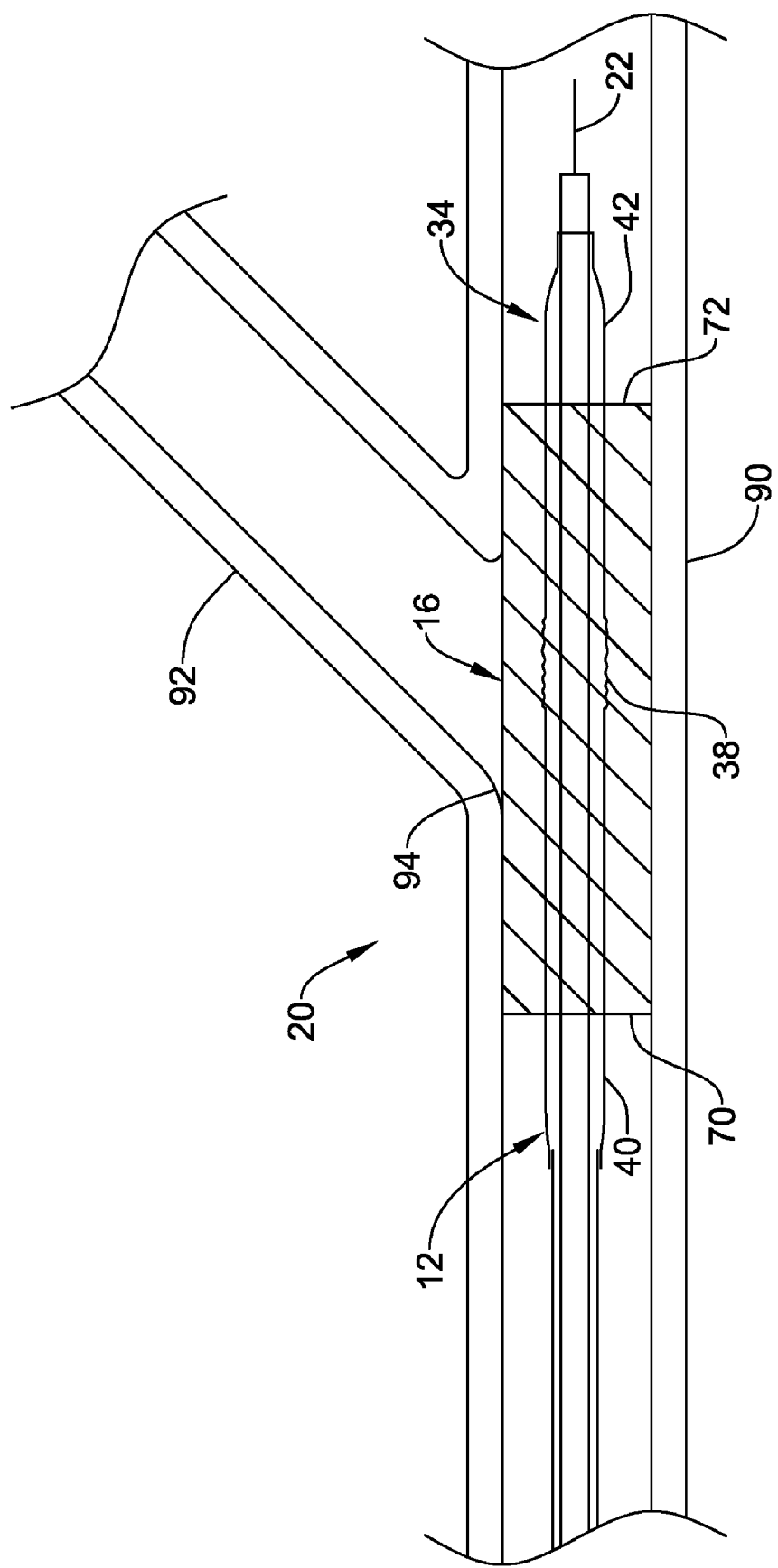

Referring now to FIG. 19, the secondary catheter branch 24 is retracted proximally over the guidewire 22 and a main catheter branch 12 is advanced over the guidewire 22 for further treatment of the vessel bifurcation 20. The main catheter branch 12 includes a balloon member 34 having a bulge portion 38. The main catheter branch 12 can be replaced with any of the catheter branches 112, 212, and variations thereof described above that define a bulge portion for expansion of a portion of the stent 16 through the ostium 94 into the branch vessel 92. The main catheter branch 12 is advanced to an axial position where the bulge portion 38 is aligned with the ostium 94 of the branch vessel 92. In some arrangements, the balloon is structured such that a proximal end 40 is positioned proximal of the proximal open end 70 of the stent 16, and a distal end portion 42 is positioned distal of the distal open end 72 of the stent 16.

Figure 20:
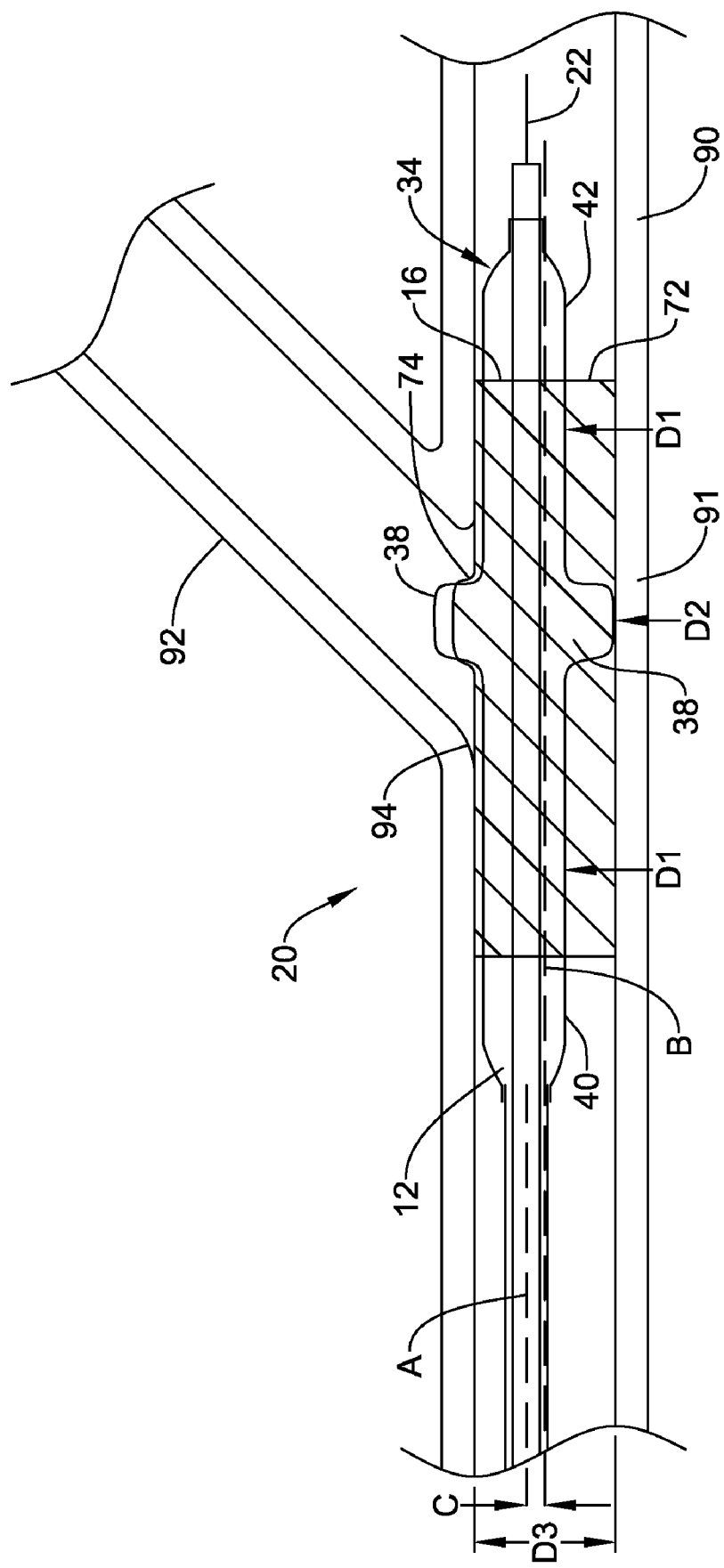

Referring now to FIG. 20, the balloon member 34 is inflated, wherein the bulge portion 38 radially expands an expandable structure zone 74 of the stent 16 radially outward into the branch vessel 92. As discussed above with reference to FIGS. 10 and 11, inflation of the bulge portion 38 of the balloon 34 causes not only radially outward expansion of strut members of the stent 16, but also provides an increased spacing between struts in the area of the ostium into the branch vessel. Increased spacing between the stent struts in the area of the ostium can provides easier navigation of a guidewire and other treatment devices through the stent sidewall and into the branch vessel 92.

The diameter D1 of the proximal and distal portions 40, 42 of the balloon member 34 is sized smaller than an internal diameter D3 of the main vessel 90. The diameter D2 of the bulge portion 38 is sized greater than the internal diameter D3 of the main vessel 90. As the balloon member 34 inflates, the main catheter branch 12 shifts towards the branch vessel 92 so that an axis A of the main catheter branch 12 is offset from a central axis B of the main vessel 90 a distance C. Shifting of the main catheter branch 12 within the main vessel 90 a distance C provides for expansion of the expandable structure zone 94 of the stent 16 into the branch vessel 90 while limiting the amount of stress applied by the bulge portion 38 on a portion 91 of the main vessel 90 opposite the ostium 94. In arrangements where the diameter D1 is substantially equal to the internal diameter D3 of the main vessel 90 and the bulge portion diameter D2 is greater than the diameters D1, D3, the bulge portion 38 could apply undesired forces and stress upon the area 91 of the main vessel 90 in addition to undesired expansion of the expandable structure zone 74 in areas other than the ostium 94 of the branch vessel 92.

Figure 21:
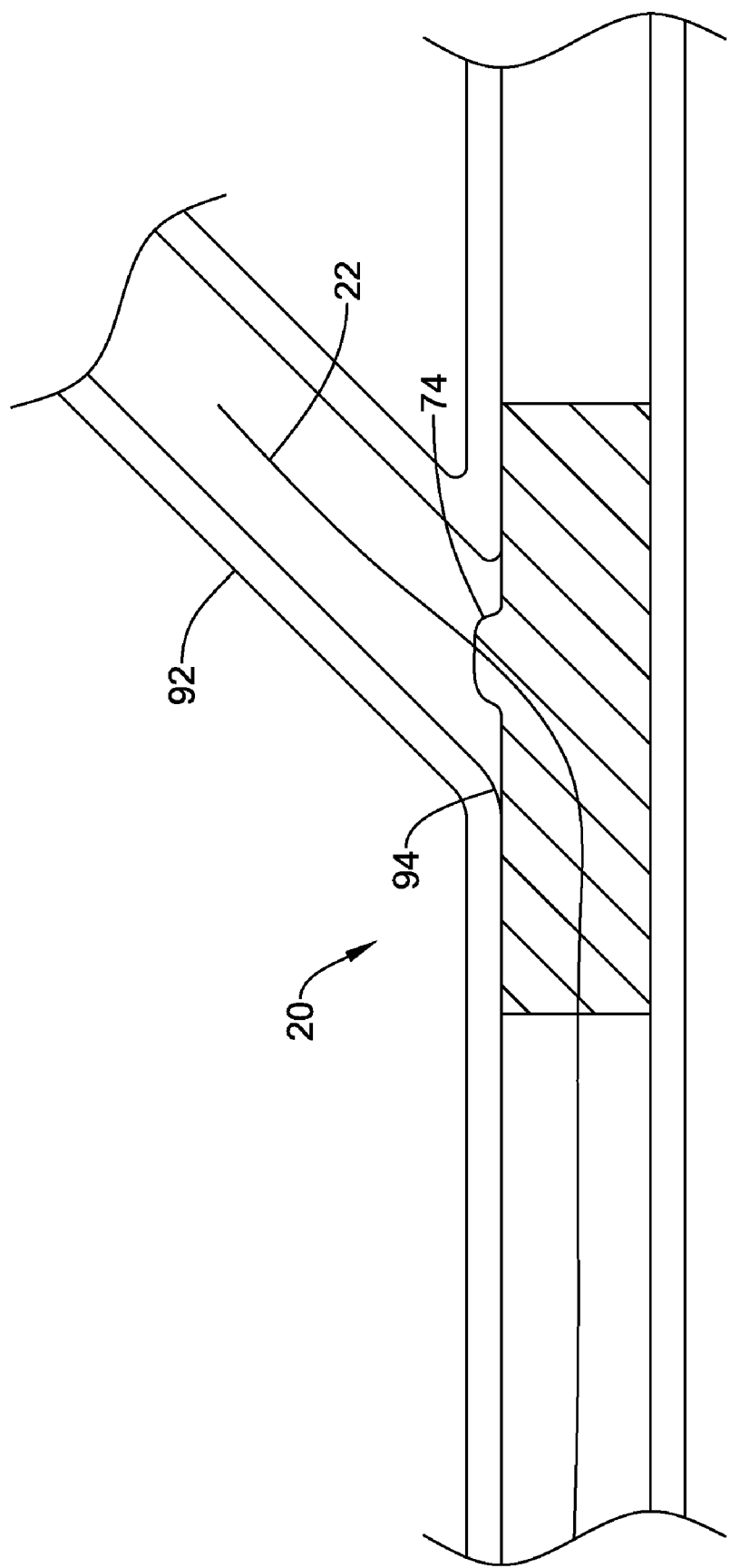
Figure 22:
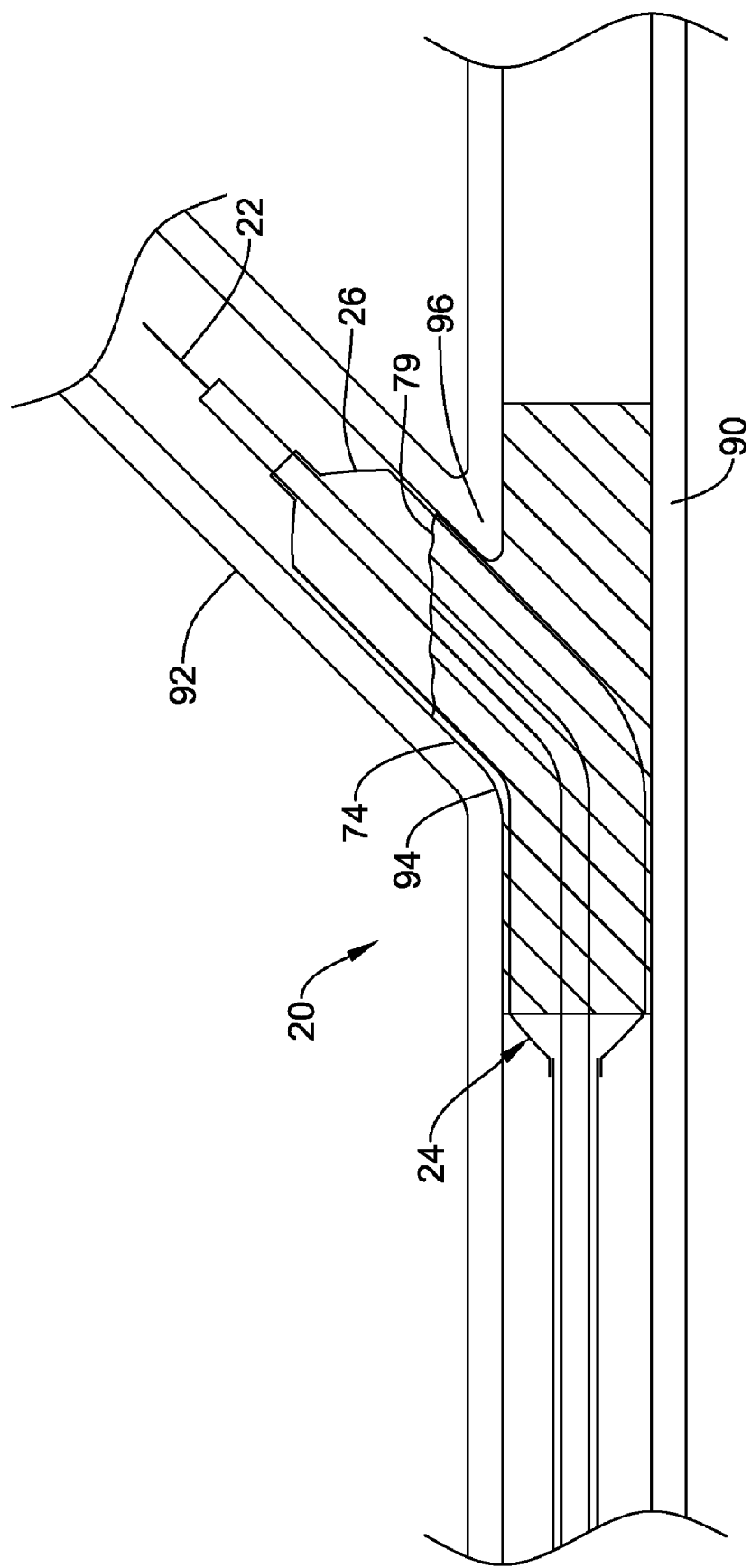

After expansion of the expandable structure zone 74 radially outward from the stent 16 into the branch vessel, which also provide spacing apart of the plurality of rows of struts in the area of the ostium 94 of the branch vessel 90, the balloon member 34 is deflated and retracted from the vessel bifurcation. Referring now to FIG. 21, the guidewire 92 can be retracted proximally to a location proximal of the expandable structure zone 74 and ostium 94 and then advanced through the expandable structure zone 74 into the branch vessel 92. With the guidewire 22 positioned within the branch vessel 92, a further treatment device, such as a secondary catheter branch 24, can be advanced along the guidewire 22, through the expandable structure zone 74 and at least partially extending into the branch vessel 92. Inflation of the secondary catheter branch 24 can further extend and expand the expandable structure zone 74 and create a side opening 79 in the stent 16. Typically, it is desirable to expand the expandable structure zone 74 sufficiently to provide engagement of the stent 16 into engagement with the carina 96 and other portions of the branch vessel 92.

Further treatment of the vessel bifurcation 20 can include deploying a branch stent within the branch vessel 92 that is advanced through a side opening 79 in the expandable structure zone 74 and at least partially overlaps the expandable structure zone 70.

The use of bulge portions 38, 138, 238 can be particularly important for moving the struts (e.g., struts 76) from the main vessel 90 into the branch vessel 92. The secondary balloon 26 typically is effective in only pushing the struts 76 towards the wall of the side branch (see FIG. 22). Usually the farther the bulge portion 38, 138, 238 can move the struts 76 into the branch vessel 90, the more effective the catheter branch 12, 112, 212 can be in helping treat the vessel bifurcation 20.

The Treatment Methods of FIGS. 23-29

FIGS. 23-30 illustrate method steps for at least partially deploying a stent 16 at a vessel bifurcation site using the main catheter branch 12 described above. While the illustrated example includes the use of main catheter branch 12 having a balloon member 34 with the bulge portion 38, main catheter branch arrangements 112, 212, and variations thereof as described above with reference to FIGS. 4-9 can also be used in the method of treating vessel bifurcation 20.

Figure 23:
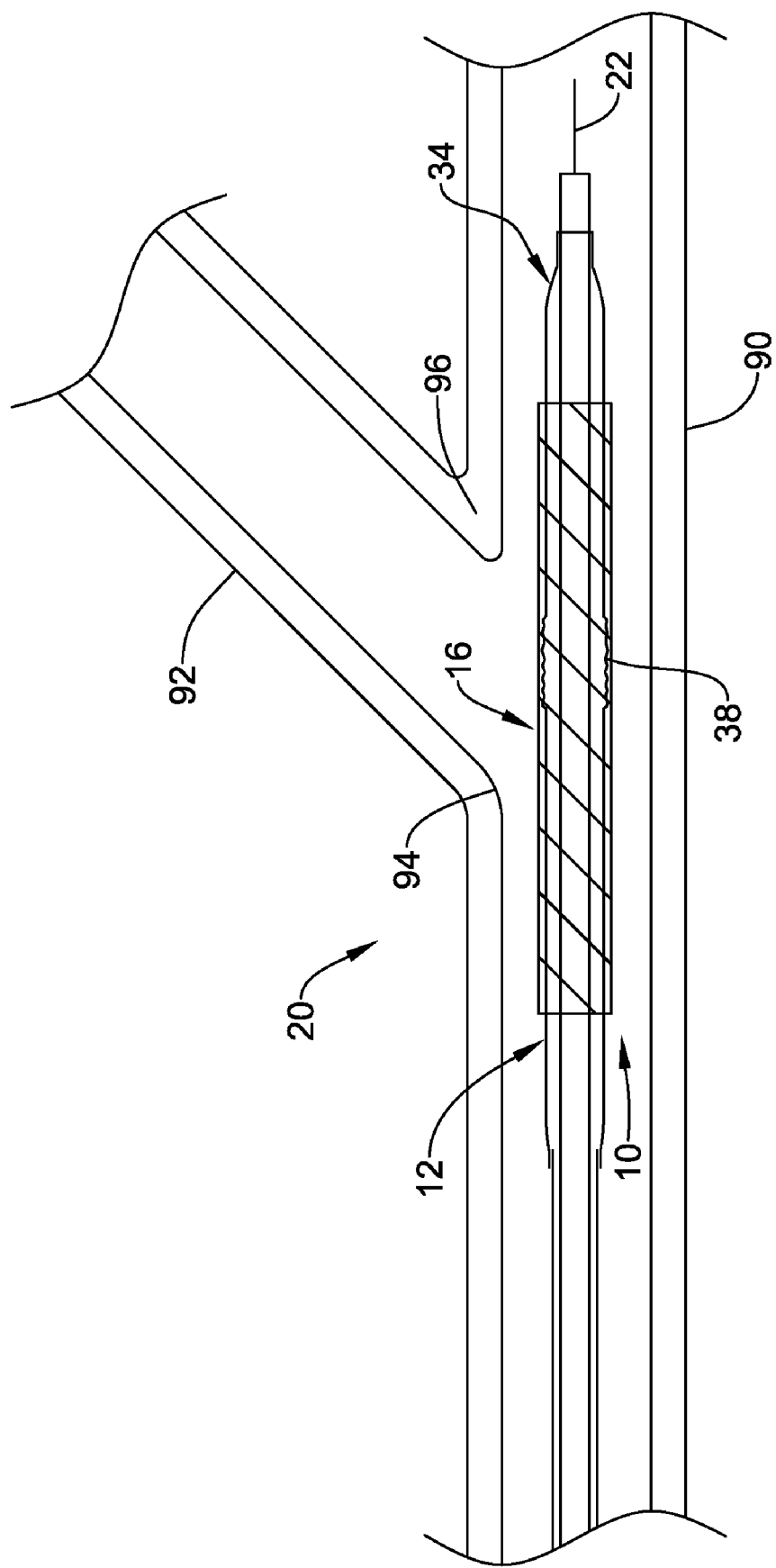
FIGS. 23-24 illustrate initial steps of several additional example methods of treating a vessel bifurcation using the balloon catheter assembly shown in FIGS. 1-3.
Figure 24:
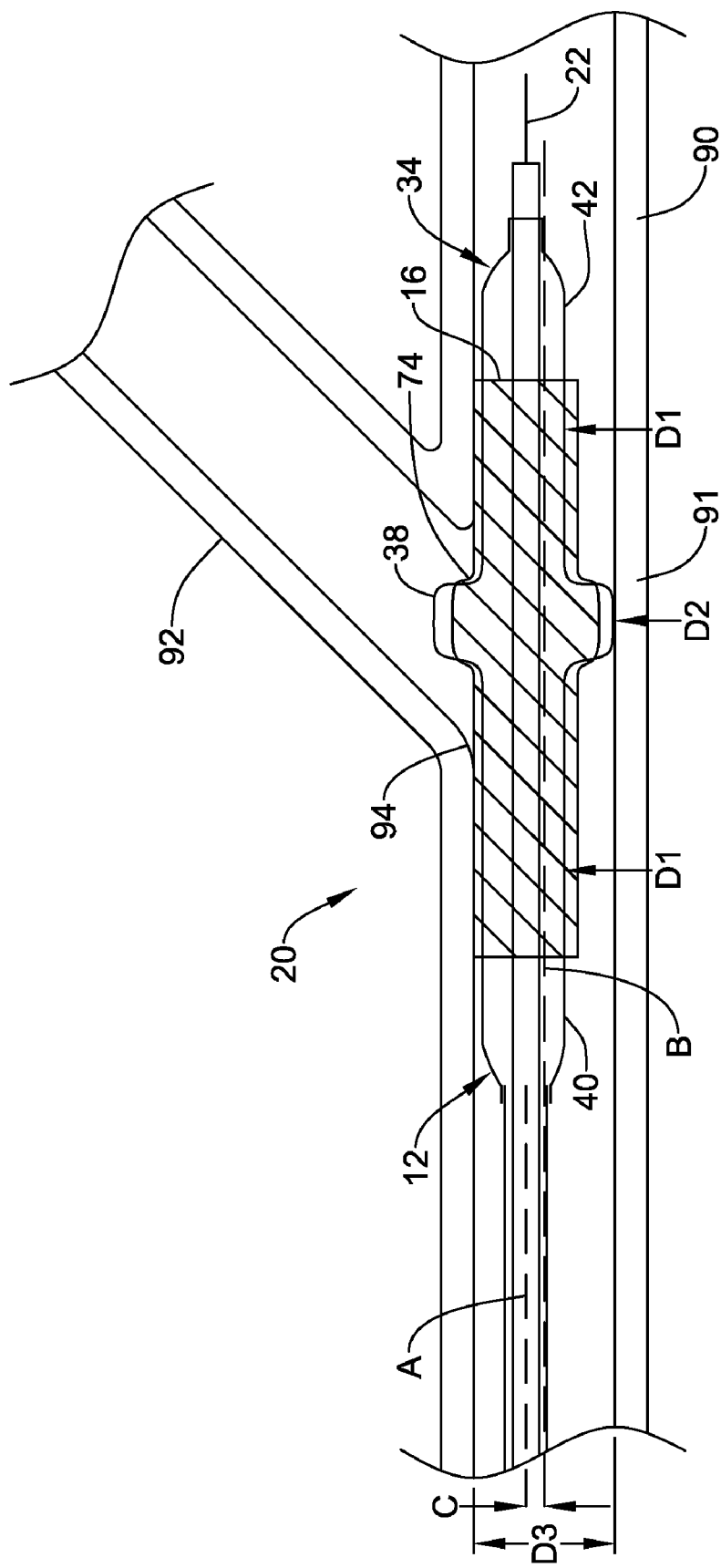

FIGS. 23-24 illustrate initial steps in the treatment methods described further with reference to FIGS. 25-27 and FIGS. 28-30. A first step of the method includes advancing a guidewire 22 within the main vessel 90 to a location spanning across the ostium 94 of the branch vessel 92 (e.g., see FIG. 16). A catheter assembly 10 is then advanced over the guidewire 22 to a position in which the bulge portion 38 of the balloon member 34 is axially aligned with the ostium 94. The balloon member 34 can be arranged at any radially rotated position relative to the ostium 94 due to the relatively constant shape and size of the bulge portion 38 around a circumference of the balloon member 34. Referring to FIG. 24, the balloon member 34 is then inflated to at least partially expand the proximal and distal portions 40, 42 of the balloon member 34 and the expandable structure zone 74.

Typically, the outer diameter D1 of the proximal and distal portions 40, 42 is less than the internal diameter D3 of the main vessel 90. The diameter D2 of the bulge portion 38 is typically greater than the diameter D3. Inflating the balloon member 34 tends to shift the main catheter branch 12 towards the branch vessel 92 a distance C defined between an axis A of the main catheter branch 12 and a central axis B of the main vessel 90. The difference in diameters D1, D3 typically results in limited engagement between the stent 16 and the main vessel 90 except in the area of expandable structure zone 74 that is expanded by the bulge portion 38. Typically, inflation of the bulge portion 38 provides expansion of the expandable structure zone 74 sufficient to create an engagement interface with the main vessel 90 that fixes the stent 16 in a radial and axial position relative to the ostium 94 without creating undue stress in the area 91 of the main vessel 90 opposite the ostium 94. After desired expansion of expandable structure zone 74 of the stent 16, the balloon member 34 can be deflated and the main catheter branch 12 retracted proximally from the patient.

Further, treatment of the vessel bifurcation 20 can be performed in different ways as described now with reference to FIGS. 25-27 and an alternative method described with reference to FIGS. 28-30.

Figure 25:
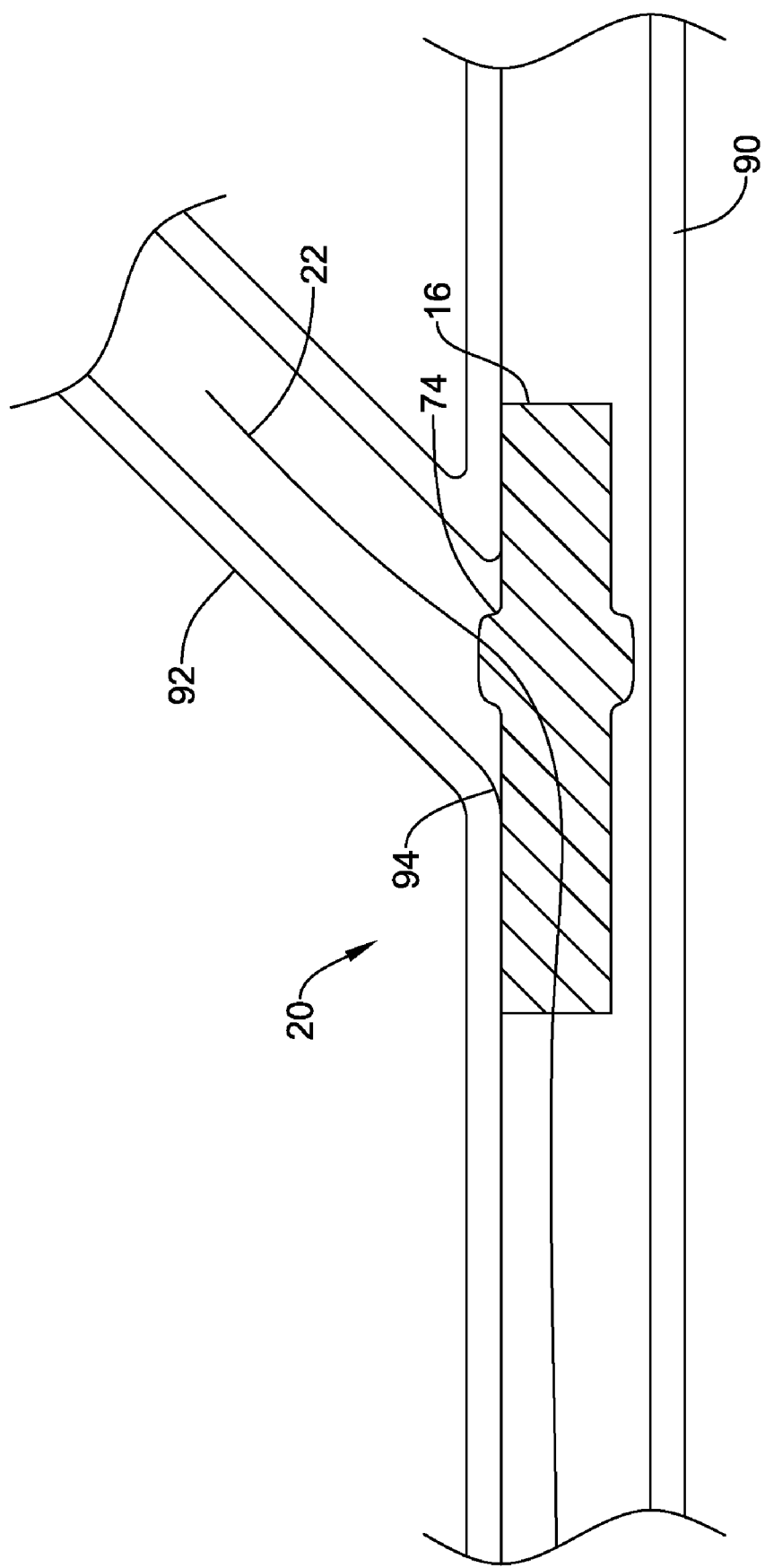
FIG. 25-27 illustrate further steps of an example method of treating a vessel bifurcation that follow the steps described with reference to FIGS. 23-24.
Figure 26:
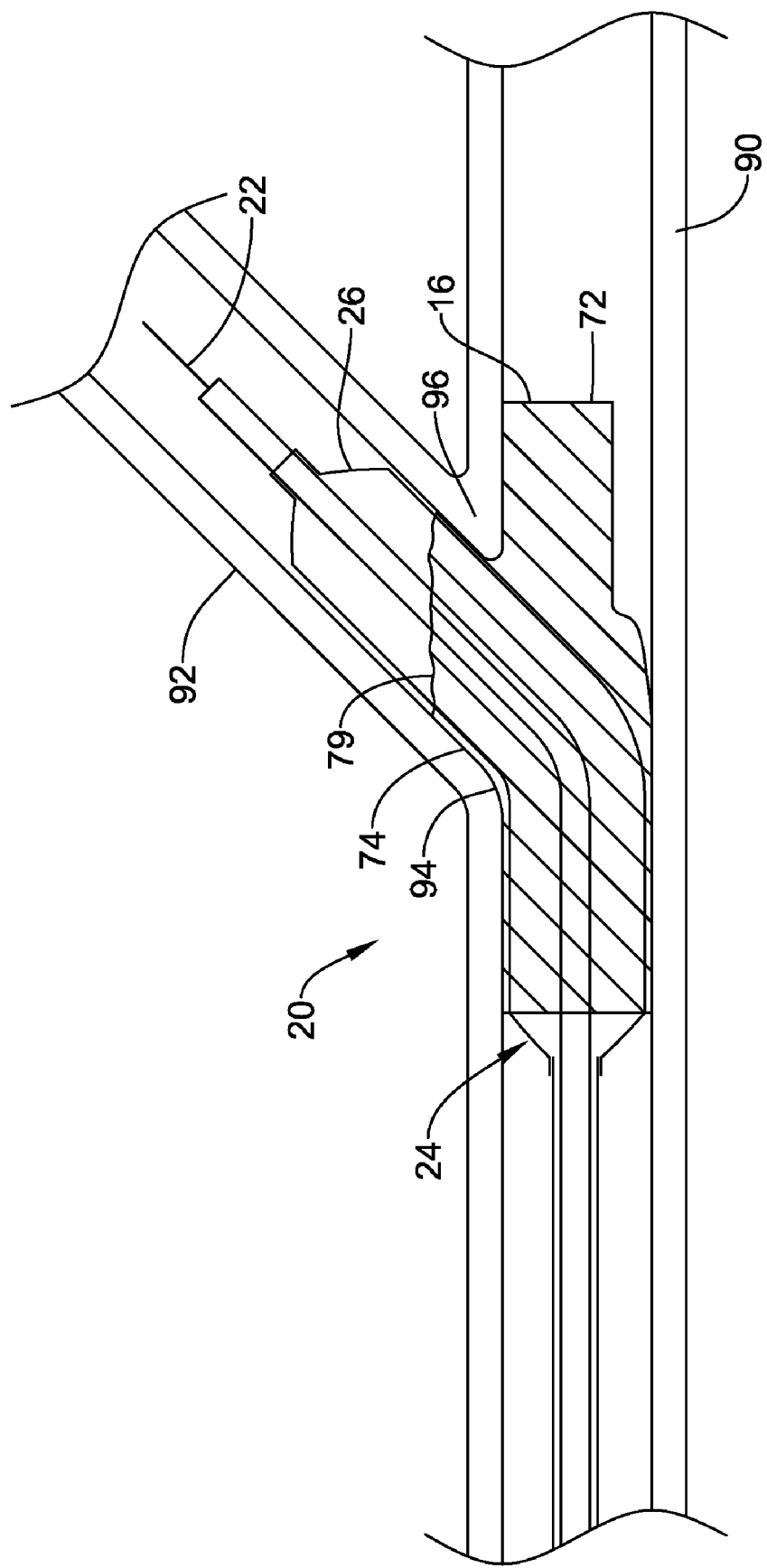
Figure 27:
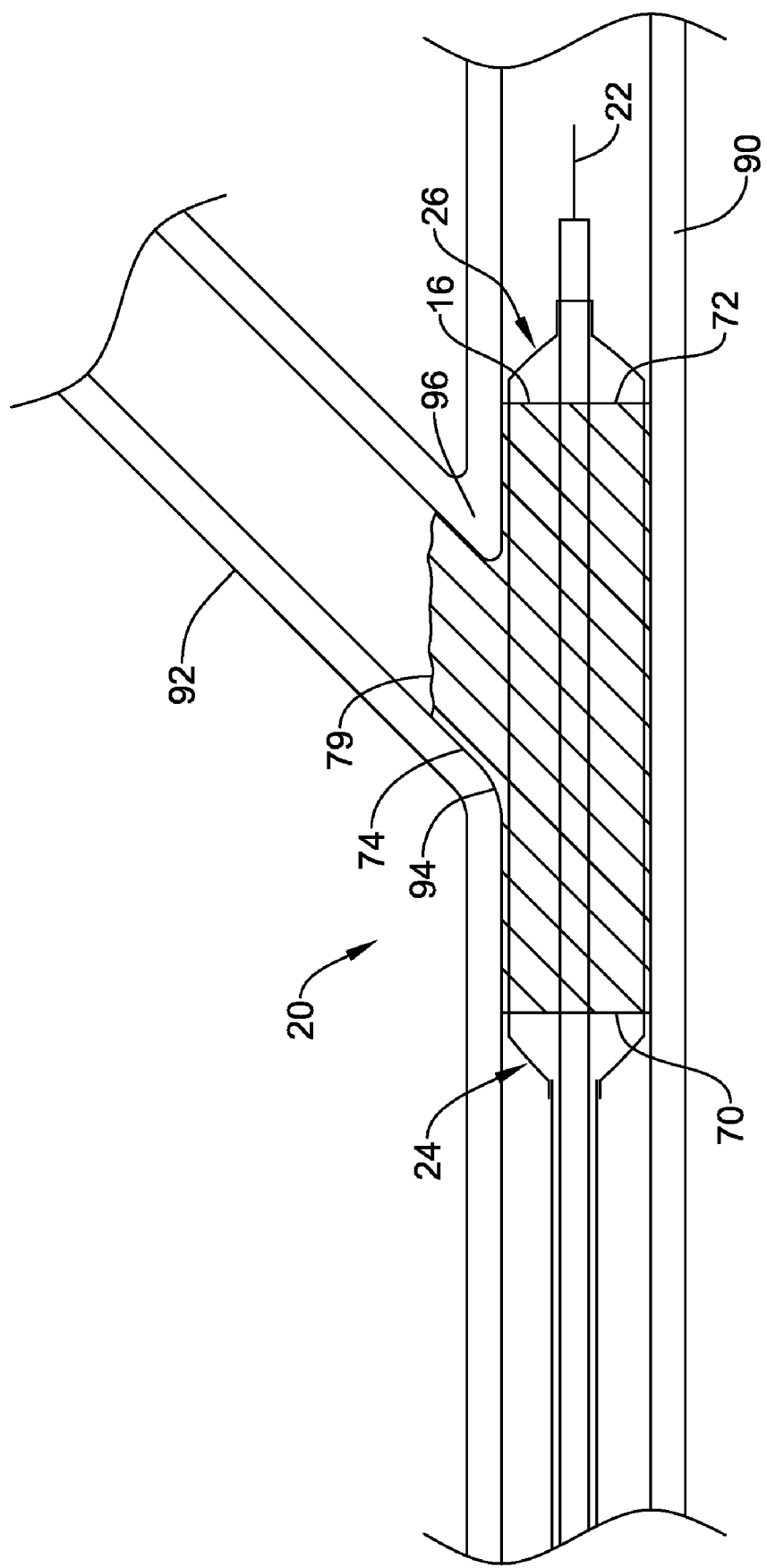

Referring now to FIGS. 25-27, after retracting the main catheter branch 12, the guidewire 22 is retracted proximally into the stent 16 and then advanced through a side wall of the stent 16 at the area of the expandable structure zone 74 and into the branch vessel 92. The use of some stent constructions, such as the example stent described with reference to FIGS. 10 and 11, can provide improved spacing between adjacent struts in the expandable structure zone 74 that provides improved ease in advancing the guidewire 22 through the stent sidewall and into the branch vessel 92.

Referring to FIG. 26, a secondary catheter branch 24 is advanced along the guidewire 22, through the expandable structure zone 74, and at least partially extending into the branch vessel 92. Inflation of the balloon 26 of the secondary catheter branch 24 creates an expanded side opening 79 in the expandable structure zone 74. Expansion of the balloon 26 can also provide engagement of the struts in the expandable structure zone 74 into engagement with portions of the branch vessel 92 such as the carina 96. Expansion of balloon 134 within that portion of the stent 16 proximal of the expandable structure zone 74 can create a side opening or aperture 79. Expansion of balloon 134 can also expand that portion of the stent 16 proximal of the expandable stent structure zone 74 into engagement with the main vessel 90 as shown in FIG. 26. That portion of the stent 16 distal of the expandable structure zone 74 can still remain in a partially expanded state that is not fully engaged with the main vessel 90.

After inflation of the balloon 26 within the branch vessel 92, the balloon 26 can be at least partially deflated and retracted proximally to a position proximal of the expandable structure zone 74. The main guidewire 22 can also be retracted proximally out of the branch vessel and side opening 79 and then advanced distally in the main vessel 90 through the distal open end 72 of the stent 16. The secondary catheter branch 24 (or an alternative balloon catheter) is then advanced along the guidewire 22 and at least partially through the distal open end 72 of the stent 16. The balloon 26 is inflated as shown in FIG. 27 to expand at least that portion of the stent 16 distal of the side opening 79 into engagement with the main vessel 90. In some arrangements, such as shown in FIG. 27, the balloon member 34 has sufficient length to span an entire length of the stent 16 from the proximal open end 40 to the distal open end 42. The balloon 26 can provide a relatively consistent expansion of the stent 16 into engagement with the main vessel 90 both proximal and distal of the side opening 79.

Figure 28:
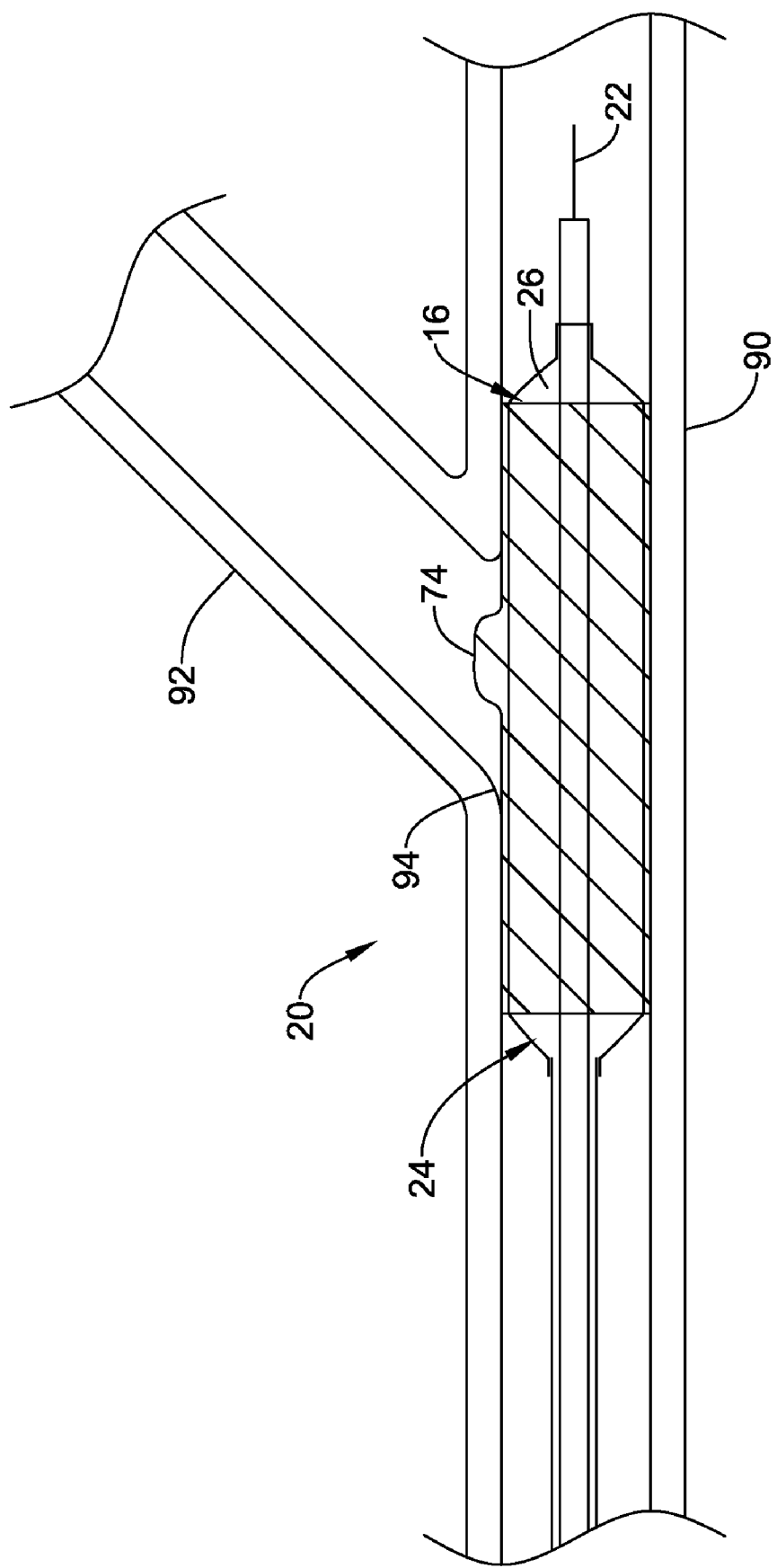
FIGS. 28-30 illustrate further steps of a further example method of treating a vessel bifurcation that follow the steps described with reference to FIGS. 23-24.
Figure 29:
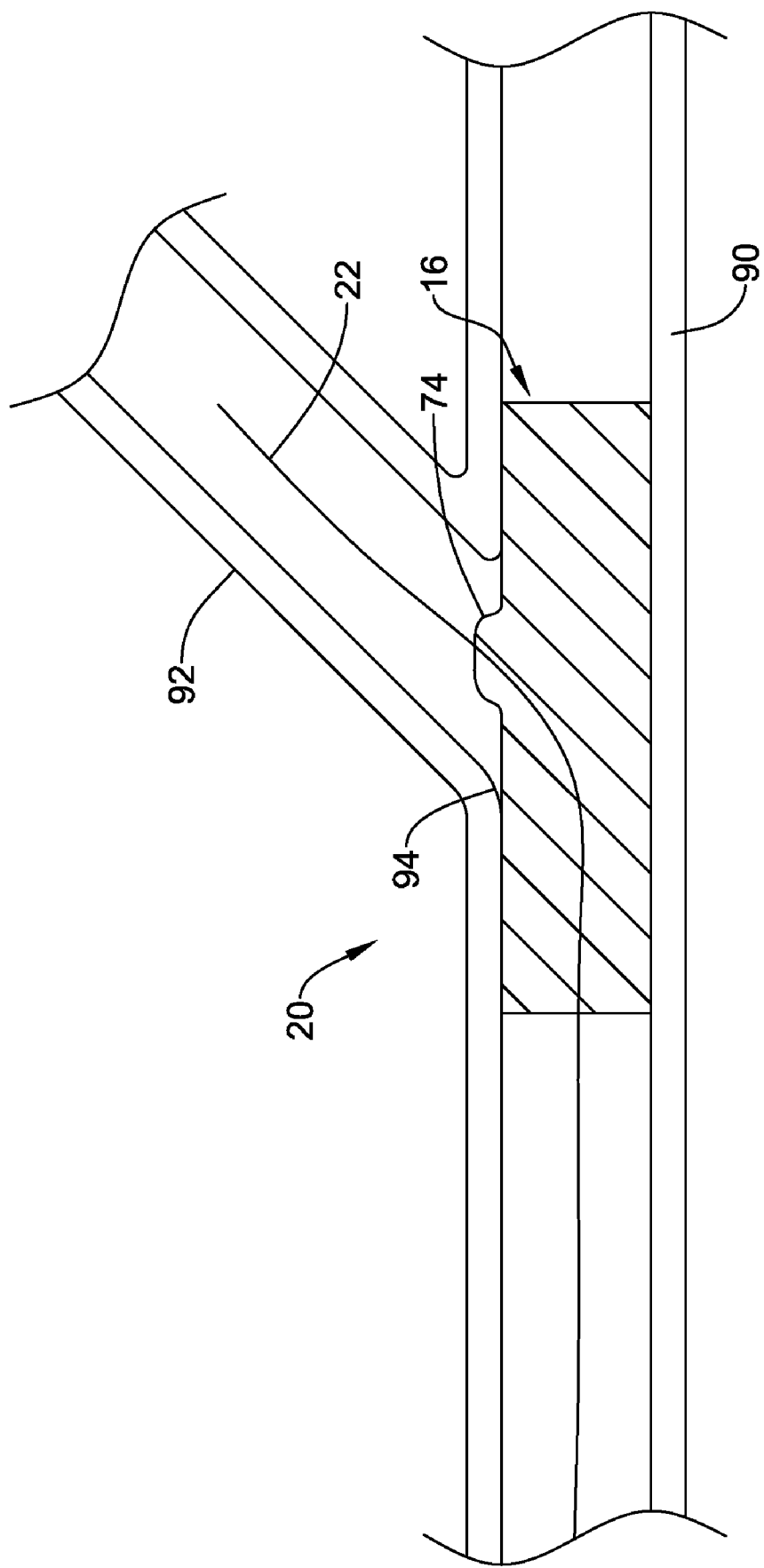
Figure 30:
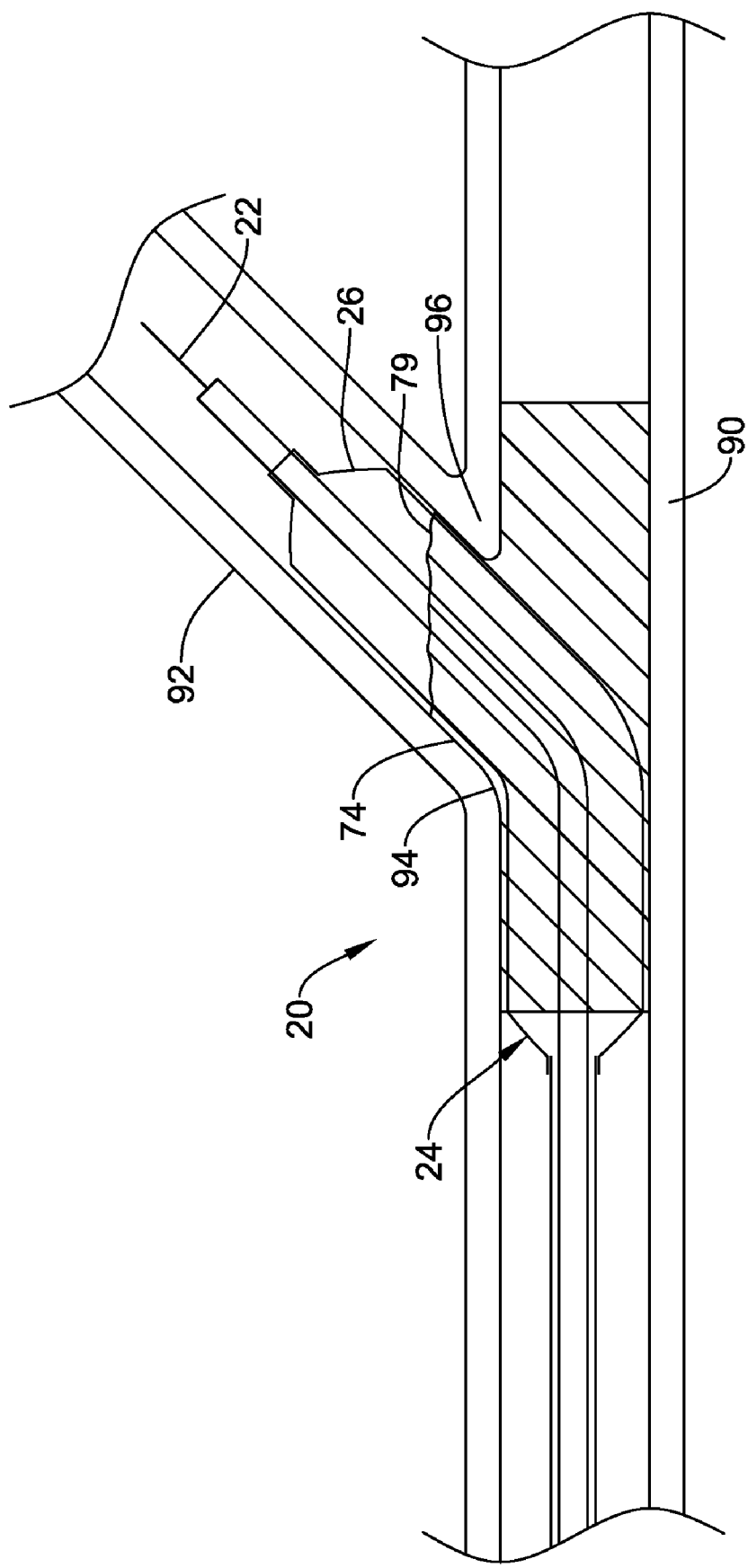

FIGS. 28-30 illustrate an alternative method of treating the vessel bifurcation 20 after the initial steps shown in FIGS. 23 and 24. After retracting proximally the main catheter branch 12, the guidewire 22 is maintained in position within the main vessel 90 and the secondary guidewire branch 24 is advanced over the main vessel guidewire 22 to span the ostium 94. The balloon 26 is then inflated to expand those portions of the stent 16 positioned proximal and distal of the expandable structure zone 74 into engagement with the main vessel 90 as shown in FIG. 28. The secondary catheter branch 24 and the guidewire 22 are then retracted proximally of the expandable structure zone 74 and the ostium 94. The guidewire 22 is advanced through the expandable structure zone 74 into the branch vessel 92. The secondary catheter branch 24 is advanced over the guidewire 22 and through the expandable structure zone 74 to extend at least partially into the branch vessel 92. The balloon 26 is then inflated as shown in FIG. 30 to further expand the expandable structure zone 74 and to create the side opening 79. Inflation balloon 26 can expand the expandable structure zone 74 into engagement with portions of the branch vessel 92 such as the carina 96.

The vessel bifurcation 20 can be additionally treated by, for example, deploying a branch stent that is positioned within the branch vessel 92 and at least partially overlapping the expandable structure zone 74 in the area of the ostium 94.

The various method systems and methods described above with reference to FIGS. 1-29 provide for treatment of a vessel bifurcation using a single guidewire. Using a single guidewire for treatment of a vessel bifurcation can reduce the complexity of the treatment process by avoiding problems that exist when using two or more guidewires (e.g., guidewire twist problems). Furthermore, the use of a balloon member having a bulge portion that extends around an entire circumference of the balloon member can have advantages as compared to the use of a balloon member having a bulge portion at a location along a length of the balloon member that must be aligned both radially and axially relative to the ostium of the branch vessel. Substantially eliminating the need for radial positioning of a bulge portion of a balloon for treatment of a vessel bifurcation can improve providing radially outward expansion of portions of the stent into the branch vessel.

Materials and Other Considerations

The materials used in the balloons and catheter shafts disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 IF, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

The sleeve members disclosed herein can be constructed of the same or similar material used for the balloons and catheter shafts disclosed herein. In some embodiments, the sleeve members can include reinforcing fibers positioned on interior or exterior surfaces, or embedded therein. Some example inelastic fibers are described in co-pending PCT Published Application No. WO 2006/042260, entitled REINFORCED AND DRUG-ELUTING BALLOON CATHETERS AND METHODS FOR MAKING SAME, which is incorporated herein by reference. The strands can be elastic or inelastic in composition. The reinforcing strands can be used to increase axial or radial stiffness of the sleeve member. The reinforcing strands can also be used to limit expansion of the sleeve member. The strands can be woven or wound, both in a single rotating or a counter-rotating direction. Example products used as reinforcing strands are 3M™ Nextel™ Continuous Ceramic Oxide Fibers 312, 440, 550, 610 and 720. Another example reinforcing strand material is a Stainless Steel Wire 316L for textile. An example Stainless Steel materials include a 35 micrometer Stainless Steel 316l product sold by I & G Trading, 9/F, Hungkuk Building, Enhaeng dong 26-1, Jung gu, Daejeon, Daejeon, South Korea, and Dyneema® fibers sold by DSM Biomedical Materials, Koestraat 1-6167 RA Geleen P.O. Box 18-6160 MD Geleen, The Netherlands.

In some embodiments, the balloon, catheter shaft, and sleeve members can be coated or eluting of biological agents or drugs. Some example biological agents and drugs appropriate for use in such applications are disclosed in U.S. Published patent Application No 2006/45901A1 and U.S. Pat. Nos. 5,304,121; 5,954,706; 6,358,556; 6,120,847; and 6,156,373, which are incorporated herein by reference. The balloon, catheter shaft, and sleeve members disclosed herein can also contain nano or micro surface structures, such as holes, pores, pockets, lattice, channels, ribs, pitted, concave or convex features, reservoirs, UV ablated surface structures and/or protrusions such as "fibers" that are finger-like in construction. The balloon, catheter shaft, and sleeve members disclosed herein can also contain processing for enhanced surface energy and coatings of drugs, biological agents, anti-coagulants, hydrophilic or hydrophobic coatings and effects.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the methods discussed above related to FIGS. 16-29 are described above using a stent construction such as the stent 16 described with reference to FIGS. 10-11, such a specialized stent construction is not always necessary. A standard stent, such as a stent construction having a consistent strut construction along the length of the stent could be used with the balloon members having the bulge portions described with reference to FIGS. 1-11. Some example standard stent constructions are disclosed in U.S. Pat. Nos. 6,913,619; 6,945,993; 7,223,283 produced by Boston Scientific Corp., which are incorporated herein by reference. Other example stents are disclosed in, for example, U.S. Pat. Nos. 6,210,429 and 6,325,826, and co-pending U.S. patent application Ser. No. 10/644,550, filed on Aug. 21, 2003, and titled STENT WITH A PROTRUDING BRANCH PORTION FOR BIFURCATED VESSELS, which are incorporated herein by reference.

CONCLUSION

One aspect of the present disclosure relates a catheter assembly that includes a stent and a catheter branch assembly. The stent defines an interior volume and has a distal open end, a proximal open end, and expandable strut structure defining a sidewall of the stent. The catheter branch assembly includes a catheter shaft having a distal end portion, and a balloon member extending from the distal end portion of the catheter shaft. The balloon member has a main body portion and a bulge portion when the balloon member is inflated. The main body portion has a distal end portion and a proximal end portion. The bulge portion is positioned at a location between the distal and proximal end portion of the main body portion. The bulge portion is configured to expand the stent in a radial outward direction relative to the sidewall of the stent when inflated.

Another aspect of the present disclosure relates to a catheter branch assembly that includes a catheter shaft having a distal end portion, a balloon member, a guidewire housing, and a sleeve. The balloon member extends from the distal end portion of the catheter shaft and includes a main body portion. The main body portion has a distal end portion and a proximal end portion. The guidewire housing extends through the catheter shaft and the balloon member. The sleeve is positioned on the balloon member and has a distal portion and a proximal portion axially spaced apart along a length of the main body portion of the balloon member. The distal and proximal portions of the sheath are configured to restrict radial expansion of the distal and proximal end portions of the maim body portion. The sleeve is configured to provide less restriction to radial expansion of that portion of the main body portion exposed at a location between the axially spaced apart distal and proximal portions of the sleeve. The sleeve can include a plurality of axially arranged slits formed therein at a position located between the proximal and distal portions thereof. The slits define a plurality of axially arranged sleeve strips.

A further aspect of the present disclosure relates to a balloon catheter that includes a catheter shaft and a balloon member. The catheter shaft has a distal end portion. The balloon member is positioned at the distal end portion of the catheter shaft and includes a main body portion and a bulge portion. The main body portion has a proximal end portion, a distal end portion, and an outer surface that defines a circumference of the main body portion. The main body portion has a maximum width dimension when the balloon member is inflated. The bulge portion is positioned at a location between the proximal and distal end portions of the main body portion. The bulge portion extends around the circumference of the main body portion and has a maximum width dimension when the balloon member is inflated that is greater than the maximum width dimension of the main body portion.

A still further aspect of the present disclosure relates to a method of expanding a stent with a catheter assembly. The catheter assembly includes a catheter branch assembly having a balloon member. The balloon member includes a main balloon portion and a bulge portion that extends around a circumference of the main balloon portion. The bulge portion has a maximum radial dimension that is greater than a maximum radial dimension of the main balloon portion. The stent is positioned on the balloon and has a main body portion and an expandable structure portion. The method includes inflating the balloon member, and expanding the expandable structure portion of the stent in a radial outward direction with the inflated bulge portion of the balloon member. The method can also include expanding the main body portion of the stent, wherein a maximum expanded dimension of the expanded expandable structure portion of the stent is greater than a maximum expanded dimension of the main body portion of the stent.

Another aspect of the present disclosure relates to a method of treating a vessel bifurcation with a catheter assembly. The catheter assembly includes a guidewire, a catheter branch, and a stent. The catheter branch includes a balloon member having a main balloon portion and a bulge portion. The bulge portion extends around a circumference of the main balloon portion and is positioned at a location between proximal and distal end portions of the main balloon portion. The stent is positioned on the balloon member in alignment with the bulge portion. The method can include advancing the guidewire into a main vessel of the vessel bifurcation distally beyond an ostium of a branch vessel of the vessel bifurcation, and advancing the catheter branch and stent over the guidewire to the vessel bifurcation with the bulge portion of the balloon member axially aligned with the ostium of the branch vessel. The method can also include inflating the balloon member to expand at least a portion of the stent through the ostium into the branch vessel, retracting the catheter branch proximally, retracting the guidewire proximal of the ostium, advancing the guidewire through the portion of the expanded stent and into the branch vessel, advancing a secondary balloon catheter over the guidewire and through the portion of the expanded stent, and further expanding the portion of the stent with the secondary balloon catheter.

A related aspect of the present disclosure relates to a method of treating a vessel bifurcation with a catheter assembly. The catheter assembly includes a guidewire, a catheter branch, and a stent. The catheter branch includes a balloon member having a main balloon portion and a bulge portion. The bulge portion extends around a circumference of the main balloon portion and is positioned at a location between proximal and distal end portions of the main balloon portion. The stent is positioned on the balloon member in alignment with the bulge portion. The method can include advancing the guidewire into a main vessel of the vessel bifurcation distally beyond an ostium of a branch vessel of the vessel bifurcation, positioning the stent in the main vessel spanning the ostium, expanding the stent into engagement with the main vessel, and advancing the catheter branch over the guidewire to the vessel bifurcation with the bulge portion of the balloon member axially aligned with the ostium of the branch vessel. The method can further include inflating the balloon member to expand at least a portion of the stent through the ostium into the branch vessel, retracting the catheter branch proximally, retracting the guidewire proximal of the ostium, advancing the guidewire through the portion of the expanded stent and into the branch vessel, advancing a secondary balloon catheter over the guidewire and through the portion of the expanded stent, and further expanding the portion of the stent with the secondary balloon catheter.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter branch assembly, comprising:
   (a) a catheter shaft having a distal end portion;
   (b) a balloon member extending from the distal end portion of the catheter shaft, the balloon member having a main body portion that, when unrestricted, has a generally constant diameter, the main body portion having a distal portion, a proximal portion, and an intermediate portion between the distal portion and the proximal portion;
   (c) a guidewire housing extending through the catheter shaft and the balloon member; and
   (d) a continuous one-piece sleeve positioned on the balloon member, at least a portion of the sleeve including a plurality of slits formed therein, the slits disposed around the circumference of the sleeve, the sleeve having a distal portion and a proximal portion axially spaced apart along a length of the main body portion of the balloon member, the distal portion and the proximal portion of the sleeve configured to expand while restricting radial expansion of the distal portion and the proximal portion of the main body portion to a first diameter, and the sleeve configured to provide less restriction to radial expansion of the intermediate portion of the main body portion positioned at a location between the axially spaced apart distal and proximal portions of the sleeve such that the intermediate portion of the main body portion expands substantially uniformly about its circumference to a second diameter that is larger than the first diameter, wherein the balloon extends proximally beyond a proximal end of the sleeve and distally beyond a distal end of the sleeve.

2. The catheter branch assembly of claim 1, wherein the plurality of slits are arranged axially at a position located between the proximal and distal portions thereof, the slits defining a plurality of axially arranged sleeve strips, wherein the sleeve strips are continuous with the proximal and distal portions of the sleeve.

3. The catheter branch assembly of claim 1, wherein the proximal portion of the sleeve has a distal end, and the distal portion of the sleeve has a proximal end, the distal end of the proximal portion being spaced apart from the proximal end of the distal portion a distance sufficient for the main body portion of the balloon member to expand radially outward relative to the sleeve to create a balloon bulge portion when the balloon member is inflated.

4. The catheter branch assembly of claim 1, wherein the plurality of slits are helical.

5. The catheter branch assembly of claim 1, wherein the sleeve includes stiffening fibers aligned along a length of the sleeve.

* * * * *